(12) United States Patent
Carraro et al.

(10) Patent No.: US 9,512,439 B2
(45) Date of Patent: Dec. 6, 2016

(54) METHODS FOR PRODUCING PROTEINS IN PLANTS

(75) Inventors: Andrea Carraro, Ins (CH); John Faulkner, Gorgier (CH); Yorick Klipfel, St-Saphorin-sur-Morges (CH); Oleg Mironov, Neuchatel (CH); Karen Oishi, Neuchatel (CH); Sandrine Roesti, Grandson (CH)

(73) Assignee: Philip Morris Products S.A., Neuchatel (CH)

( * ) Notice: Subject to any disclaimer, the term of this patent is extended or adjusted under 35 U.S.C. 154(b) by 485 days.

(21) Appl. No.: 13/809,995

(22) PCT Filed: Jul. 15, 2011

(86) PCT No.: PCT/EP2011/062180
§ 371 (c)(1),
(2), (4) Date: Feb. 28, 2013

(87) PCT Pub. No.: WO2012/007587
PCT Pub. Date: Jan. 19, 2012

(65) Prior Publication Data
US 2013/0205448 A1    Aug. 8, 2013

(30) Foreign Application Priority Data

Jul. 16, 2010 (EP) .................................. 10169888

(51) Int. Cl.
| | | |
|---|---|---|
| C12M 1/00 | (2006.01) | |
| C12N 15/82 | (2006.01) | |
| A01G 7/00 | (2006.01) | |

(52) U.S. Cl.
CPC ............. *C12N 15/8251* (2013.01); *A01G 7/00* (2013.01); *C12N 15/8205* (2013.01)

(58) Field of Classification Search
CPC .... A01G 7/00; C12N 15/8205; C12N 15/8251
See application file for complete search history.

(56) References Cited

U.S. PATENT DOCUMENTS 5,611,172 A * 3/1997 Dugan et al. .............. 47/1.01 R
2005/0246786 A1* 11/2005 Adams et al. ................ 800/278
(Continued)

FOREIGN PATENT DOCUMENTS

| EP | 1 662 002 | 5/2006 |
|---|---|---|
| EP | 1662002 | 5/2006 |

(Continued)

OTHER PUBLICATIONS

Singapore Search Report and Written Opinion for Application No. 201300206-8 dated May 9, 2014 (18 pages). English translation included.

(Continued)

*Primary Examiner* — Michael Hobbs
(74) *Attorney, Agent, or Firm* — Mueting, Raasch & Gebhardt, P.A.

(57) ABSTRACT

The present invention relates to methods for expressing proteins of interest, particularly pharmaceutically valuable proteins, transiently in plants. In particular, the invention provides an improved method for introducing *Agrobacterium* cells into a whole plant or a plant organ. The methods of the invention provides efficient agroinfiltration of many plants singly or simultaneously resulting in a yield of recombinant proteins that is higher than that obtained by other methods. The methods can be readily scaled and automated to meet changing demands of the recombinant protein.

24 Claims, 5 Drawing Sheets

(56) References Cited

U.S. PATENT DOCUMENTS

2007/0136898 A1* 6/2007 Ishida ................ 800/294
2011/0174447 A1* 7/2011 Duesel et al. ............ 159/4.02

FOREIGN PATENT DOCUMENTS

| EP | 2 085 481 | 8/2009 | | |
|---|---|---|---|---|
| WO | 99/48355 | 9/1999 | | |
| WO | 01/12828 | 2/2001 | | |
| WO | WO 2005/017169 | 2/2005 | | |
| WO | WO 2005/071090 | 8/2005 | | |
| WO | WO 2009/011726 | 1/2009 | | |
| WO | WO2009/095183 A1 * | 8/2009 | ............. | C12N 15/82 |

OTHER PUBLICATIONS

Chinese Office Action for Application No. 201180039815-5 dated Jan. 23, 2014 (19 pages). English translation included.

Grimsley, "Agroinfection", *Methods in Molecular Biology*, vol. 44, Agrobacterium Protocols, 1995, pp. 325-342.

Kapila, "An Agrobacterium-Mediated Transient Gene Expression System for Intact Leaves", *Plant Science*, vol. 122, No. 1, Jan. 15, 1997, pp. 101-108.

PCT/EP2011/062180 Search Report and Written Opinion dated Aug. 23, 2011.

Office Action issued in Russia for Application No. 2013106842/10 dated Dec. 11, 2015, 8 pages. English translation included.

European Office Action for Application No. 11735855.6-1410 dated Jun. 8, 2015 (5 pages).

Andrieu et al., "An in planta, Agrobacterium-mediated transient gene expression method for inducing gene silencing in rice (*Oryza sativa* l.) leaves", *RICE*, vol. 5, No. 1, 31 Aug. 2012 , pp. 1-13.

Office Action issued in Japan for Application No. 2013-520087 dated Sep. 7, 2015 (11 pages). English translation included.

* cited by examiner

METHODS FOR PRODUCING PROTEINS IN PLANTS

This application is a U.S. National Stage Application of International Application No. PCT/EP2011/062180, filed Jul. 15, 2011, which was published in English on Jan. 19, 2012 as International Patent Publication WO 2012-007587 A1. International Application No. PCT/EP2011/062180 also claims priority to European Application No. 10169888.4, filed Jul. 16, 2010.

The present invention relates to methods for expressing proteins of interest, particularly pharmaceutically valuable proteins, transiently in plants.

The large scale production of recombinant proteins is an important application of transgenic plants. Although many plants can be successfully used for production of recombinant proteins, few systems have the potential to produce substantial amounts of a recombinant protein within a short time period.

Transient gene expression in plant cells has been developed as a rapid means to produce small amounts of a given protein and for testing genetic constructs. Methods to transiently produce a protein in a plant cell include for example particle gun delivery of a nucleic acid molecule comprising the gene coding for a desired protein in an expressible manner, *Agrobacterium*-mediated delivery of a binary vector comprising the expressible gene, electroporation of protoplasts, and polyethylene glycol-mediated delivery of naked DNA into plant protoplasts.

Particle bombardment usually reaches only a few cells and the DNA must reach the cell nucleus for transcription to be accomplished, and is thus not very efficient for transient expression.

The use of *Agrobacterium* delivered by infiltration (agroinfiltration) can deliver foreign genes to significantly higher number of cells. The original system of *Agrobacterium* infiltration for transient expression was described by Kapila et al., Plant Sci. 122: 101-108 (1997) and was developed for rapid testing of the functionality of a protein thought to be useful for disease resistance of the plant tissue. For this application the protein would not need to be purified or characterized since the entire plant tissue could be used in a bioassay. This system was later used to express pharmaceutically important proteins (Vaquero et al., Mol. Biotechnol. 5: 209-21 (1996)). However, the production from this system was relatively low.

WO 99/48355 discloses a method of genetic transformation of plants including the steps of (a) immersing plant tissue in a medium including an infective transformation vector such as *Agrobacterium*; (b) reducing the pressure on said tissue to −10 to −100 kPa gauge; (c) maintaining said pressure for 10 to 60 minutes, and (d) raising said pressure to atmospheric pressure or above, wherein the transformation vector allows selection to identify plant cells or tissues in which the transformation vector is integrated into the genome said plant tissues or cells. It is further disclosed that the plant material may be subjected to alternating cycles of reduced and over pressure, wherein the pressure is set forth to be in a range of 10 to 500 kPa (0.1 to 5 bar).

EP 1 662 002 discloses methods for *Agrobacterium*-mediated gene transduction and transformation comprising preparing plant material, infecting the plant material with *Agrobacterium* carrying a vector containing a desired transgene. It is further part of the method to pressurize the plant material during the process of preparing the plant material, or after preparation, but before infection with the *Agrobacteria*.

WO 01/12828 describes an apparatus that comprises a vacuum chamber, means for generating a vacuum, and a connector between the vacuum generating means and the vacuum chamber and, further, means for affixing or supporting a plant inside the vacuum chamber.

There is a need for systems and methods that can produce a substantial amount of a recombinant protein at a commercial scale within a short time period, such as for example, subunit vaccines for the prevention of pandemic outbreaks or emerging diseases.

The present invention provides the means and methods to meet this need. In particular, the present invention provides in one embodiment a method for producing a heterologous peptide or protein of interest comprising:
  (i) contacting a whole plant, particularly a whole and intact plant or a part of a whole and intact plant, or a plurality of whole and intact plants or a plurality of parts of whole and intact plants, with *Agrobacterium* cells suspended in a fluid, wherein the *Agrobacterium* cells comprise an expressible, particularly a plant expressible construct encoding the heterologous peptide or protein of interest;
  (ii) treating said plant or plant part, or the plurality of plants or plant parts and the *Agrobacterium* cells with one or more pressure cycle(s) whereby the *Agrobacterium* cells infiltrate the whole plant or the plant part, and
wherein the expressible construct is selected to provide transient expression of the heterologous peptide or protein of interest and at least one of the pressure cycles comprises an increase in pressure relative to atmospheric pressure.

In certain embodiments of the invention, the plants are treated with one or more pressure cycles, which all comprise an increase in pressure relative to atmospheric pressure.

In a specific embodiment, the pressure per cycle is maintained for a period of between 0.5 seconds and 60 seconds.

In one embodiment, the present invention provides a method for infiltrating *Agrobacteria* into a plant or plant part, or a plurality of plants or plant parts, comprising:
  (i) contacting a whole plant, particularly a whole and intact plant or a part of a whole and intact plant, or a plurality of whole and intact plants or a plurality of parts of whole and intact plants, with *Agrobacterium* cells suspended in a fluid;
  (ii) treating said plant or plant part, or the plurality of plants or plant parts and the *Agrobacterium* cells with one or more pressure cycle(s),
wherein the expressible construct is selected to provide transient expression of the heterologous peptide or protein of interest and at least one of the pressure cycles comprises an increase in pressure relative to atmospheric pressure.

In certain embodiments of the invention, the plants are treated with one or more pressure cycles, which all comprise an increase in pressure relative to atmospheric pressure.

In a specific embodiment, the pressure per cycle is maintained for a period of between 0.5 seconds and 60 seconds.

In one embodiment of the invention, the whole plant, particularly the whole and intact plant or a part of the whole and intact plant, or the plurality of whole and intact plants or of parts of whole and intact plants, and the *Agrobacterium* cells are treated with one or more pressure cycle(s) within a closed system, particularly a system comprising a chamber configured for receiving a whole plant, particularly a whole and intact plant or a part of the whole and intact plant, and a means for adjustably increasing air and/or fluid pressure in the chamber.

In one embodiment of the invention, the chamber is configured such that the entire plant body including its aerial and underground parts is submerged in the infiltration medium containing the *Argobacterium* cells and subjected to the pressure applied during the one or more pressure cycle(s).

In another embodiment of the invention, the chamber is configured such that only all or part of the aerial parts of the plant are submerged in the infiltration medium containing the *Argobacterium* cells, but the entire plant including the aerial parts as well as the underground parts of the plant is subjected to the pressure applied during the one or more pressure cycle(s).

In still another embodiment of the invention, the chamber is configured such that all or part of the aerial parts of the plant are submerged in the infiltration medium containing the *Argobacterium* cells and exposed to pressure in the one or more pressure cycles, whereas the underground parts of the plant, particularly the plant root, are positioned outside of the chamber such that they are not submerged in the infiltration medium containing the *Agrobacterium* cells and not subjected to the pressure applied during the one or more pressure cycle(s).

In one embodiment of the invention, the pressure treatment comprising one or more pressure cycle(s) is applied to the whole and intact plant or a part of the whole and intact plant, while said plant or plant part is in contact with the *Agrobacterium* cells in the bacterial cell suspension.

In one embodiment of the invention, the suspension of *Agrobacterium* cells comprises an OD600 of at least 1.0, particularly of at least 1.5, particularly of at least 2.0, particularly of at least 2.5, particularly of at least 3.0, particularly of at least 3.5, particularly of at least 4.0, particularly of at least 4.5.

In one embodiment of the invention, at least one of the pressure cycles comprises subjecting the whole plant, particularly the whole and intact plant or a part of the whole and intact plant, or the plurality of whole and intact plants or of parts of whole and intact plants, to a pressure which is increased relative to atmospheric pressure, particularly the whole and intact plant or a part of the whole and intact plant is subjected to a pressure of at least 0.5 bar, particularly of at least 1.0 bar, particularly of at least 1.5 bar, particularly of at least 2.0 bar, particularly of at least 2.5 bar, particularly of at least 3.0 bar, particularly of at least 3.5 bar, particularly of at least 4.0 bar, particularly of at least 4.5 bar, particularly of at least 5.0 bar, particularly of at least 5.5 bar, particularly of at least 6.0 bar, particularly of at least 7.0 bar, particularly of at least 8.0 bar, particularly of at least 9.0 bar, particularly of at least 10.0 bar, particularly of at least 11.0 bar, and particularly of at least 12.0 bar.

The optimal pressure, which allows a maximal infiltration of the bacterial suspension into the plant or plant part without damaging the plant, may vary depending on the plant species and, within a given plant species, also depending on the variety, used in the infiltration method. The optimal pressure conditions can be easily determined by the person skilled in the art by using a test system as disclosed herein in the Examples.

In one embodiment of the invention, the step of treating the whole plant, particularly the whole and intact plant or a part of the whole and intact plant, or the plurality of whole and intact plants or of parts of whole and intact plants, comprises at least 2 cycles, particularly at least 3 cycles, particularly at least 4 cycles, particularly at least 5 cycles, particularly at least 6 cycles, particularly at least 7 cycles, particularly at least 8 cycles, particularly at least 9 cycles, particularly at least 10 cycles, particularly at least 11 cycles, wherein at least one of said cycles, or, in a specific embodiment, all of said cycles, comprise a pressure of at least 0.5 bar, particularly of at least 1.0 bar, particularly of at least 1.5 bar, particularly of at least 2.0 bar, particularly of at least 2.5 bar, particularly of at least 3.0 bar, particularly of at least 3.5 bar, particularly of at least 4.0 bar, particularly of at least 4.5 bar, particularly of at least 5.0 bar, particularly of at least 5.5 bar, particularly of at least 6.0 bar, for at least 0.1 seconds/cycle, particularly for at least 0.2 second/cycle, particularly for at least 0.3 second/cycle, particularly for at least 0.4 second/cycle, particularly for at least 0.5 second/cycle, particularly for at least 1 second/cycle, particularly for at least 1.5 seconds/cycle, particularly for at least 2.0 seconds/cycle, particularly for at least 2.5 seconds/cycle, particularly for at least 3.0 seconds/cycle, particularly for at least 3.5 seconds/cycle, particularly for at least 5.0 seconds/cycle.

In one embodiment of the invention, the step of treating the whole plant or the plurality of whole plants, or the plant part or the plurality of plant parts comprises at least 2 cycles.

In one embodiment of the invention, the step of treating the whole plant or the plurality of whole plants or the plant part or the plurality of plant parts comprises at least 4 cycles.

In one embodiment of the invention, the step of treating the whole plant or the plurality of whole plants or the plant part or the plurality of plant parts comprises at least 5 cycles.

In one embodiment of the invention, the step of treating the whole plant or the plurality of whole plants or the plant part or the plurality of plant parts comprises at least 6 cycles.

In one embodiment of the invention, the step of treating the whole plant or the plurality of whole plants or the plant part or the plurality of plant parts comprises at least 7 cycles.

In one embodiment of the invention, the step of treating the whole plant or the plurality of whole plants or the plant part or the plurality of plant parts comprises at least 8 cycles.

In one embodiment of the invention, at least one of the pressure cycles comprises treating the whole plant or the plurality of whole plants or the plant part or the plurality of plant parts, with a pressure of at least 2.5 bar.

In one embodiment of the invention, at least one of the pressure cycles comprises treating the whole plant or the plurality of whole plants or the plant part or the plurality of plant parts, with a pressure of at least 3.5 bar.

In one embodiment of the invention, at least one of the pressure cycles comprises treating the whole plant or the plurality of whole plants or the plant part or the plurality of plant parts, with a pressure of at least 4.5 bar.

In one embodiment of the invention, at least one of the pressure cycles comprises treating the whole plant or the plurality of whole plants or the plant part or the plurality of plant parts, with a pressure of at least 6 bar.

In one embodiment of the invention, at least one of the pressure cycles comprises treating the whole plant or the plurality of whole plants or the plant part or the plurality of plant parts, with a pressure of at least 8 bar.

In one embodiment of the invention, at least one of the pressure cycles comprises treating the whole plant or the plurality of whole plants or the plant part or the plurality of plant parts, with a pressure of at least 12 bar.

In one embodiment of the invention, the pressure is applied for between 0.5 seconds/cycle and 10 seconds/cycle.

In one embodiment of the invention, the pressure is applied for between 1 second/cycle and 5 seconds/cycle.

In one embodiment of the invention, the pressure is applied for between 0.5 seconds/cycle and 1 second/cycle.

In one embodiment of the invention, the step of treating the whole plant, particularly the whole and intact plant or a part of the whole and intact plant, or the plurality of whole and intact plants or of parts of whole and intact plants, with a pressure that is increased relative to atmospheric pressure comprises at least 5 cycles, at a pressure of at least 3.0 bar, for at least 0.5 seconds/cycle.

In one embodiment of the invention, the step of treating the whole plant, particularly the whole and intact plant or a part of the whole and intact plant, or the plurality of whole and intact plants or of parts of whole and intact plants, with a pressure that is increased relative to atmospheric pressure comprises at least 8 cycles, at a pressure of at least 4.5 bar, for at least 1 second/cycle.

In one embodiment of the invention, the step of treating the whole plant, particularly the whole and intact plant or a part of the whole and intact plant, or the plurality of whole and intact plants or of parts of whole and intact plants, with a pressure that is increased relative to atmospheric pressure comprises at least 1 cycle, at a pressure of at least 8.0 bar, for at least 0.5 seconds/cycle.

In one embodiment of the invention, the step of treating the whole plant, particularly the whole and intact plant or a part of the whole and intact plant, or the plurality of whole and intact plants or of parts of whole and intact plants, with a pressure that is increased relative to atmospheric pressure comprises at least 2 cycles, at a pressure of at least 6.0 bar, for at least 0.5 seconds/cycle.

In one embodiment of the invention, the step of contacting the whole plant, particularly the whole and intact plant or a part of the whole and intact plant, or the plurality of whole and intact plants or of parts of whole and intact plants, with *Agrobacterium* cells comprises (i) dipping the plant or a part thereof in a suspension of *Agrobacterium* cells, wherein the suspension comprises an OD600 of at least 1.0, particularly of at least 1.5, particularly of at least 2.0, particularly of at least 2.5, particularly of at least 3.0, particularly of at least 3.5, particularly of at least 4.0, particularly of at least 4.5, (ii) exposing the plant or a part thereof to an aerosol generated by using a suspension of *Agrobacterium* cells comprising an OD600 of at least 1.0, particularly of at least 1.5, particularly of at least 2.0, particularly of at least 2.5, particularly of at least 3.0, particularly of at least 3.5, particularly of at least 4.0, particularly of at least 4.5.

In one embodiment of the invention, the plant is a *Nicotiana* species, particularly a *Nicotiana tabacum* species, at a development stage of 8, 9, or 10.

In one embodiment, the present invention provides a system for infiltrating *Agrobacteria* into a whole plant, particularly a whole and intact plant or a part of a whole and intact plant, or a plurality of whole and intact plants or of parts of whole and intact plants, and/or for producing a heterologous peptide or protein comprising a chamber configured for receiving a whole plant, particularly a whole and intact plant or a part of a plant, and a means configured for adjustably increasing air and/or fluid pressure in the chamber.

In one embodiment of the invention, the system comprises a compressor and a pressure reducer.

In one embodiment of the invention, the system comprises a plurality of inlets, outlets and conduits for providing a fluid path between the interior and exterior of the chamber, wherein the flow of fluid is regulated.

In one embodiment of the invention, the chamber comprises, in the interior, a plurality of nozzles that are dimensioned for atomizing or aerosolizing a liquid.

In one embodiment of the invention, the chamber is configured such that the entire plant body including its aerial and underground parts is submerged in the infiltration medium containing the *Argobacterium* cells and subjected to the pressure applied during the one or more pressure cycle(s).

In one embodiment of the invention, the chamber is configured such that only all or part of the aerial parts of the plant are submerged in the infiltration medium containing the *Argobacterium* cells, but the entire plant including the aerial parts as well as the underground parts of the plant is subjected to the pressure applied during the one or more pressure cycle(s).

In one embodiment of the invention, the chamber is configured such that all or part of the aerial parts of the plant are submerged in the infiltration medium containing the *Argobacterium* cells and exposed to pressure in the one or more pressure cycles, whereas the underground parts of the plant, particularly the plant root, are positioned outside of the chamber such that they are not submerged in the infiltration medium containing the *Agrobacterium* cells and not subjected to the pressure applied during the one or more pressure cycle(s).

In one embodiment of the invention, the chamber comprises one or more openings to allow passage of aerial parts of the plants during insertion or removal, which openings are lined with an elastic seal, particularly an elastic pneumatic or hydraulic seal.

In one embodiment, the invention relates to the use of a system according to the invention and as described herein for infiltrating *Agrobacterium* bacteria into a whole plant, particularly a whole and intact plant or a plant part and/or for producing a heterologous peptide or protein.

DEFINITIONS

The technical terms and expressions used within the scope of this application are generally to be given the meaning commonly applied to them in the pertinent art of plant biology.

All of the following term definitions apply to the complete content of this application. The word "comprising" does not exclude other elements or steps, and the indefinite article "a" or "an" does not exclude a plurality. A single step may fulfil the functions of several features recited in the claims. The terms "essentially", "about", "approximately" and the like in connection with an attribute or a value particularly also define exactly the attribute or exactly the value, respectively. The term "about" in the context of a given numerate value or range refers to a value or range that is within 20%, within 10%, within 5%, or within 2% of the given value or range.

A "plant" as used within the present invention refers to an intact plant, a substantially intact plant, or to a plurality of intact or substantially intact plants; a whole plant, a substantially whole plant, or a plurality of whole or substantially whole plants, and its progenies, at any stage of its development. For the purpose of the present application, an intact plant is understood to refer to a plant comprising an essentially intact and closed vascular system, which does not show drainage of the vascular fluids due to injury or lesions.

A "plant part" as used within the present invention refers to a any part of a plant including cuttings, a plant organ, a plant tissue, or a plant cell, which plant part may be an isolated part of the plant or a part of the whole and intact plant.

A "part of a whole and intact plant" is meant to refer to a plant part that even if infiltrated separately from the remaining part of the plant is provided as a functional component of the plant with a vascular system that remains fully integrated into the intact and closed vascular system of the intact plant.

A "plant cell" as used within the present invention refers to a structural and physiological unit of a plant including pollen, ovules, and zygotes. The plant cell may be in form of a protoplast without a cell wall, an isolated single cell, a cultured cell, or a cell as a part of higher organized unit such as, but not limited to, plant tissue, a plant organ, or a whole plant, including a whole and intact plant.

"Plant tissue" as used herein means a plurality of plant cells that are organized into structural or functional units. This includes any tissue of a plant in planta or in culture.

"Plant organ" as used herein refers to a distinct or a differentiated part of a plant such as but not limited to a root, stem, leaf, flower, flower part, flower bud, embryos, seeds or fruits. This includes any organ of a plant in planta or in culture.

"Plant material" as used within the present invention refers to any solid, liquid or gaseous composition, or a combination thereof, including but not limited to secretions or extracts, obtainable from a plant, its tissues and organs either in planta or in culture, including leaves, stems, roots, flowers or flower parts, fruits, pollen, ovules, zygotes, seeds, cuttings, and any other parts of a plant.

"Plant cell culture" as used within the present invention encompasses cultures of plant cells such as but not limited to, protoplasts, cell culture cells, cells in cultured plant tissues, cells in explants, and pollen cultures.

A "tobacco plant" as used within the present invention refers to a plant of a species belonging to the genus *Nicotiana*, including but not limited to *Nicotiana tabacum* (or *N. tabacum*). Certain embodiments of the invention are described herein using the term "tobacco plant" without specifying *Nicotiana tabacum*, such descriptions are to be construed to have included *Nicotiana tabacum* specifically.

The term "polynucleotide" is used herein to refer to a polymer of nucleotides, which may be unmodified or modified deoxyribonucleic acid (DNA) or ribonucleic acid (RNA). Accordingly, a polynucleotide can be, without limitation, a genomic DNA, complementary DNA (cDNA), mRNA, or antisense RNA. Moreover, a polynucleotide can be single-stranded or double-stranded DNA, DNA that is a mixture of single-stranded and double-stranded regions, a hybrid molecule comprising DNA and RNA, or a hybrid molecule with a mixture of single-stranded and double-stranded regions. In addition, the polynucleotide can be composed of triple-stranded regions comprising DNA, RNA, or both. A polynucleotide can contain one or more modified bases, such as phosphothioates, and can be a peptide nucleic acid (PNA). Generally, polynucleotides provided by this invention can be assembled from isolated or cloned fragments of cDNA, genome DNA, oligonucleotides, or individual nucleotides, or a combination of the foregoing.

The term "nucleotide sequence" refers to the base sequence of a polymer of nucleotides, including but not limited to ribonucleotides and deoxyribonucleotides.

The term "gene sequence" as used herein refers to the nucleotide sequence of a nucleic acid molecule or polynucleotide that encodes a polypeptide or a biologically active RNA, and encompasses the nucleotide sequence of a partial coding sequence that only encodes a fragment of a protein. A gene sequence can also include sequences having a regulatory function on expression of a gene that are located upstream or downstream relative to the coding sequence, and intron sequences of a gene.

The term "promoter" refers to the nucleotide sequence at the 5' end of a gene that directs the initiation of transcription of the gene. Generally, promoter sequences are necessary, but not always sufficient, to drive the expression of a gene to which it is operably linked. In the design of an expressible gene construct, the gene is placed in sufficient proximity to and in a suitable orientation relative to a promoter such that the expression of the gene is controlled by the promoter sequence. The promoter is positioned preferentially upstream to the gene and at a distance from the transcription start site that approximates the distance between the promoter and the gene it controls in its natural setting. As is known in the art, some variation in this distance can be tolerated without loss of promoter function. As used herein, the term "operatively linked" means that a promoter is connected to a coding region in such a way that the transcription of that coding region is controlled and regulated by that promoter. Means for operatively linking a promoter to a coding region are well known in the art.

As used herein, an "expression control sequence" includes a promoter and may include, but is not limited to: one or more enhancer sequences, transcription termination sequences, polyadenylation sequences, 3' or 5' untranslated sequences, intronic sequences, ribosome binding sites, and other sequences that may stabilize or otherwise control expression of a gene in a plant cell. Expression control sequences may be endogenous (i.e., naturally found in a plant host) or exogenous (not naturally found in a plant host). Exogenous expression sequences may or may not be plant sequences so long as they are functional in a plant cell under selected conditions.

A "heterologous gene" or "heterologous coding sequence" refers to a gene or coding sequence that is exogenous to, or not naturally found in, the plant to be transformed or treated and that encodes a "heterologous polypeptide" or a biologically active fragment thereof. Heterologous gene sequences include viral, prokaryotic, and eukaryotic sequences. Prokaryotic encoding sequences include, but are not limited to, microbial sequences, bacterial sequences or viral sequences (e.g., for the production of antigens which may be administered as vaccines). Eukaryotic coding sequences include mammalian or human sequences, but may also include sequences from non-mammals, even other plants, including but not limited to leader or secretion signal sequences, targeting sequences, and the like. In one preferred aspect, a heterologous gene nucleic acid encodes a human protein. The term "heterologous gene" or "heterologous coding sequence" includes, but is not limited to, naturally occurring, mutated, variant, chemically synthesized, genomic, cDNA, or any combination of such sequences. The reference to a "gene" encompasses full-length genes or fragments thereof encoding biologically active proteins.

The term "heterologous peptide" or "heterologous protein", as used herein, refers to a peptide, including oligo- and polypeptides, or a protein that is expressed from a "heterologous gene" or heterologous coding sequence" as defined above. Accordingly, the "heterologous peptide" or "heterologous protein" produced in a plant is exogenous to, or not naturally found in, the plant. The "heterologous peptide" or "heterologous protein" can be a mammalian or human peptide or protein. The "heterologous peptide" or "heterologous protein" may even be a plant peptide or protein if it is a variant or mutated from of a plant peptide or protein or a peptide or protein not naturally found in the producing plant species, line or variety.

As used herein, a "T DNA border" refers to a DNA fragment comprising an about 25 nucleotide long sequence capable of being recognized by the virulence gene products of an *Agrobacterium* strain, such as an *A. tumefaciens* or *A. rhizogenes* strain, or a modified or mutated form thereof, and which is sufficient for transfer of a DNA sequence to which it is linked, to eukaryotic cells, preferably plant cells. This definition includes, but is not limited to, all naturally occurring T-DNA borders from wild-type Ti plasmids, as well as any functional derivative thereof, and includes chemically synthesized T-DNA borders. In one aspect, the encoding sequence and expression control sequence of an expression construct according to the invention is located between two T-DNA borders.

The term "selected to provide transient expression" refers to an expression construct that has been specifically designed for transient gene expression in plants, in particular by removing elements of conventional binary vectors necessary for stable transformation such as transformation selection genes (see, e.g., R P Hellens et al, Plant Methods 205, 1: 13).

As used herein, the term "surfactant" refers to a surface-active agent that generally comprises a hydrophobic portion and a hydrophilic portion (see, e.g., Bhairi, A Guide to the Properties and Uses of Detergents in Biological Systems, Calbiochem-Novabiochem Corp. 1997).

Surfactants may be categorized as anionic, nonionic, zwitterionic, or cationic, depending on whether they comprise one or more charged groups. Anionic surfactants contain a negatively charged group and have a net negative charge. Nonionic surfactants contain non-charged polar groups and have no charge. These surfactants are generally the reaction products of alkylene oxide with alkyl phenol, or primary or secondary alcohols, or are amine oxides, phosphine oxides or dialkyl sulphoxides.

Surfactants that can be suitably used in plant infiltration systems are, for example, disclosed in WO/2005/076766.

In particular, exemplary nonionic surfactants include, but are not limited to: t-(Triton X-100), polyoxyethylenesorbitan monolaurate (Tween 20), polyoxyethylenesorbitan monolaurate (Tween 21), polyoxyethylenesorbitan monopalmitate (Tween 40), polyoxyethylenesorbitan monostearate (Tween 60), polyoxyethylenesorbitan monooleate (Tween 80), polyoxyethylenesorbitan monotrioleate (Tween 85), (octylphenoxy) polyethoxyethanol (IGEPAL CA-630/NP-40), triethyleneglycol monolauryl ether (Brij 30), and sorbitan monolaurate (Span 20).

A zwitterionic surfactant contains both a positively charged group and a negatively charged group, and has no net charge. Suitable zwitterionic surfactants include, but are not limited to: betaines, such as carboxybetaines, sulfobetaines (also known as sultaines), amidobetaines and sulfoamidobetaines, such may comprise C8-C18, preferably C1o-C18, alkyl betaines, sulfobetaines, amidobetaines, and sulfoamidobetaines, for example, laurylamidopropylbetaine (LAB) type-betaines, n-alkyldimethylammonio methane carboxylate (DAMC), n-alkyldimethylammonio ethane carboxylate (DAEC) and n-alkyldimethylammonio propane carboxylate (DAPC), n-alkylsultaines, n-alkyl dimethylammonio alkyl sulfonates, N-alkyl dimethylammonio ethane sulfonate (DAES), n-alkyl dimethylammonio propane sulfonate (DAPS) and n-alkyl dimethylammonio butane sulfonate (DABS), hexadecyl dimethylammonio propane sulfonate, n-alkylamidomethane dimethylammonio methane carboxylates, n-alkylamido methane dimethylammonio ethane carboxylate, laurylamidopropylbetaine (LAB), n-alkylamidomethane dimethylammonio methane sulfonate, n-alkylamidoethane dimethylammonio ethane sulfonate and n-alkylamidopropane dimethylammonio propane sulfonate, 3-[(3-cholamidopropyl)dimethylammonio]-1-propane-sulfonate (CHAPS), and 3-[(3-cholamidopropyl)dimethylammonio]-2-hydroxy-1-propanesulfonate (CHAPSO), phospholipids (e.g., phosphatidylethanolamines, phosphatidylglycerols, phosphatidylinositols, diacyl phosphatidyl-cholines, dialkyl phosphatidylcholines, lysophosphatidylcholines, lysophosphatidylethanolamines, lysophosphatidylglycerols, lysophosphatidylinositols, saturated and unsaturated fatty acid derivatives (e.g., ethyl esters, propyl esters, cholesteryl esters, coenzyme A esters, nitrophenyl esters, naphtyl esters, monoglycerids, diglycerids, and triglycerides, fatty alcohols, fatty alcohol acetates, and the like), lipopolysaccharides, glyco- and shpingolipids (e.g., ceramides, cerebrosides, galactosyldiglycerids, gangliosides, lactocerebrosides, lysosulfatides, and the like).

A "cationic surfactant" has a positively charged group under the conditions of infiltration. Suitable cationic surfactants include, but are not limited to: quaternary amines or tertiary amines. Exemplary quaternary amine surfactants include, but are not limited to, cetylpyridinium chloride, cetyltrimethylammonium bromide (CTAB; Calbiochem #B22633 or Aldrich # 85582-0), cetyltrimethylammonium chloride (CTAC1; Aldrich # 29273-7), dodecyltrimethylammonium bromide (DTAB, Sigma # D-8638), dodecyltrimethylammonium chloride (DTACI), octyl trimethyl ammonium bromide, tetradecyltrimethylammonium bromide (TTAB), tetradecyltrimethylammonium chloride (TTACI), dodecylethyldimethylammonium bromide (DEDTAB), decyltrimethylammonium bromide (D10TAB), dodecyltriphenylphosphonium bromide (DTPB), octadecylyl trimethyl ammonium bromide, stearoalkonium chloride, olealkonium chloride, cetrimonium chloride, alkyl trimethyl ammonium methosulfate, palmitamidopropyl trimethyl chloride, quaternium 84 (Mackemium NLE; Mcintyre Group, Ltd.), and wheat lipid epoxide (Mackernium WLE; Mcintyre Group, Ltd.).

Exemplary ternary amine surfactants include, but are not limited to, octyldimethylamine, decyldimethylamine, dodecyldimethylamine, tetradecyldimethylamine, hexadecyldimethylamine, octyldecyldimethylamine, octyidecylmethylamine, didecylmethylamine, dodecylmethylamine, triacetylammonium chloride, cetrimonium chloride, and alkyl dimethyl benzyl ammonium chloride. Additional classes of cationic surfactants include, but are not limited to: phosphonium, imidzoline, and ethylated amine groups.

Anionic surfactants are generally water-soluble alkali metal salts of organic sulfates and sulfonates. These include, but are not limited to: potassium laurate, sodium lauryl sulfate, sodium dodecylsulfate, alkyl polyoxyethylene sulfates, sodium alginate, dioctyl sodium suifosuccinate, phosphatidyl choline, phosphatidyl glycerol, phosphatidyl inosine, phosphatidylserine, phosphatidic acid and their salts, glyceryl esters, sodium carboxymethylcellulose, cholic acid and other bile acids (e.g., cholic acid, deoxycholic acid, glycocholic acid, taurocholic acid, glycodeoxycholic acid) and salts thereof (e.g., sodium deoxycholate, etc.).

Co-surfactants such as a short-chain alcohol such as ethanol, 1-propanol, and 1-butanol, may additionally be used.

Combinations of any of the above surfactants may be used. Surfactants not specifically listed above are further encompassed within the scope of the invention.

Amounts of surfactants used will vary with the type of surfactant and plant tissue being treated (i.e., the thickness of the wax covered surface of a leaf, etc.).

Generally, surfactants are used in concentrations ranging from 0.005% to about 1% of the volume of the *Agrobacterium* suspension. Preferably, concentrations range from 0.005% to about 0.5%, and more preferably, from about 0.005% to about 0.05%. Generally, lower levels of ionic surfactants will be used than nonionic surfactants.

The term "vacuum infiltration", as used herein, relates to a method that allows the penetration of pathogenic bacteria, e.g. *Agrobacterium*, into the intercellular or interstitial spaces and in that way to study the interaction between plants and pathogenic bacteria. Physically, vacuum generates a negative atmospheric pressure that causes the air spaces between the cells in the plant tissue to decrease. The longer the duration and the lower the pressure of the vacuum, the less air space there is within the plant tissue. An increase in the pressure allows the infiltration medium, including the infective transformation vector, to relocate into the plant tissue. For plant transformation, vacuum can be applied to a plant part in the presence of *Agrobacterium* for a certain time period.

As used herein, the term "atmospheric pressure" defines a force per unit area exerted against a surface by the weight of air above that surface in the Earth's atmosphere. Pressure is a force, or weight, exerted on a surface per unit area, and is measured in Pascals (Pa). The pressure exerted by a kilogram mass on a surface equals 9.8 Pa. The pressure exerted by the whole atmosphere on the Earth's surface is approximately 100,000 Pa. Usually, atmospheric pressure is quoted in millibars (mb). 1 mb is equal to 100 Pa, so standard atmospheric pressure is about 1000 mb. In fact, actual values of atmospheric pressure vary depending on the location, altitude and weather conditions. At sea level, commonly observed values range between 970 mb and 1040 mb. Because pressure decreases with altitude, pressure observed at various locations must be adjusted to the same level, usually sea level.

A pressure exerted on an enclosed fluid at rest in a closed container, is transmitted without loss to every portion of the fluid and to the walls of the container. For a fluid at rest the difference in pressure between two points in it depends only upon the density of the fluid and the difference in depth between the two points. Accordingly, a fluid exerts a pressure on all bodies immersed in it, which is equal to the externally applied pressure on the top of the fluid plus the static fluid pressure from the weight of the liquid.

Technical and scientific terms used herein have the meanings commonly understood by one of ordinary skill in the art to which the present invention pertains, unless otherwise defined. Reference is made herein to various methodologies known to those of skill in the art. Publications and other materials setting forth such known methodologies to which reference is made are incorporated herein by reference in their entireties as though set forth in full. The practice of the invention will employ, unless otherwise indicated, conventional techniques of chemistry, molecular biology, microbiology, and plant biology, which are within the skill of the art.

Any suitable materials and/or methods known to those of skill can be utilized in carrying out the present invention: however, preferred materials and/or methods are described. Materials, reagents and the like to which reference is made in the following description and examples are obtainable from commercial sources, unless otherwise noted.

The present invention relates to systems and methods for expressing peptides and/or proteins of interest, particularly for expressing pharmaceutically valuable peptides and/or proteins, transiently in plants. In particular, the invention provides an improved method for introducing *Agrobacterium* cells into a whole and intact plant, or a plurality of whole plants, or a part of a whole and intact plant including a plant organ or tissue in planta. The method of the invention provides efficient agroinfiltration of many plants singly or simultaneously resulting in a yield of recombinant proteins that is higher than that obtained by other methods. The methods can be readily scaled and automated to meet changing demands of the recombinant protein.

Agroinfiltration of plants is currently performed according to one of these two methods.

The first method uses a syringe filled with a suspension of *Agrobacterium* cells, and injecting each individual leaf with bacteria. The syringe is positioned on the underside of the leaf, and the plunger is gently pushed such that the bacteria suspension spreads throughout the leaf. This method is laborious and not amenable to scaling up.

The second method involves using a vacuum to assist the uptake of the bacteria by the plant. Typically, a plant is placed upside down inside a chamber and its leaves are wholly immersed in a bacterial suspension. The pressure in the chamber is brought to about a few tenths of millibar. The air is initially withdrawn from the leaf by the vacuum, and when air is reintroduced, the leaf draws in the liquid. The vacuum process has at least two disadvantages, it is slow as it takes several minutes to bring the pressure down to a desirably low pressure. The vacuum generates certain non-negligible stress on the infiltrated plants that results in the plants having difficulties to recover from or to survive the infiltration process.

In one aspect, the invention provides an improved method for introducing *Agrobacterium* cells into a whole plant, or a plurality of whole plants, particularly a whole and intact plant or part of a whole and intact plant including a plant organ or plant tissue in planta. The method of the invention provides positive fluid pressure, or a combination or positive and negative fluid pressure, to facilitate *Agrobacterium* cells to infiltrate a whole plant, or the plurality of whole plants, particularly a whole and intact plant or a part of a whole and intact plant including a plant organ or plant tissue in planta, unlike methods known in the art which use a vacuum or negative pressure. The invention also provides systems and means for delivering positive fluid pressure to whole plants, or a plurality of whole plants, particularly whole and intact plants or a part of a whole and intact plant including plant organs or plant tissues in planta that are or have been contacted with *Agrobacterium* cells.

According to the invention, positive fluid pressure is delivered when the whole plant, or the plurality of whole plants, particularly the whole and intact plant or a part of the whole and intact plant, and bacteria are subjected to treatment with one or more pressure cycle(s) under closed conditions. Fluid pressure is the pressure at some point within a fluid, such as water or air. For example, under a closed condition, the volume in which the fluid is contained is constant. In various embodiments of the invention, specifications of the fluid pressure refer to the air pressure within a chamber of a fixed volume.

A fluid pressure is referred to as a positive pressure when it is greater than the ambient air pressure outside of the closed system, at the location where the method of the invention is practiced. Positive pressure or overpressure is provided when the whole plant, or the plurality of whole plants, particularly the whole and intact plant or a part of the whole and intact plant including a plant organ or plant tissue in planta, and bacteria have been exposed to a target pressure that is higher than ambient air pressure. The terms overpressure and positive pressure are herein used interchangeably.

Ambient air pressure varies depending on the altitude at the location where the method is practiced and on the weather conditions at the time when the method is practiced, and can be readily determined by techniques and equipment known in the art.

Many units can be used to express the value of a pressure. For example, the bar is a unit of pressure equal to 100 kilopascal, and roughly equal to the atmospheric pressure on Earth at sea level. Atmospheric air pressure is often given in millibars where standard sea level pressure (1 atm) is defined as 1013.25 mbar (hPa), equal to 1.01325 bar.

Positive pressure values useful in the invention can thus be expressed in terms of a percentage value of the ambient air pressure, for example and without limitation, 110%, 125%, 150%, 175%, 200%, 250%, 300%, 350%, 400%, 350%, 500%, 550%, 600%, 650%, 700%, 750%, 800%, 850%, 900%, 950%, 1000%, 1050%, 1110%, 1150%, 1200%, or any intermediate value, or any value greater than the foregoing. A similar convention can be used for describing negative pressure which is a pressure value lower than the ambient air pressure.

A positive pressure can alternatively be expressed in terms of an absolute value, for example and without limitation, 1.1 atm, 1.5 atm, 2 atm, 2.5 atm, 3 atm, 3.5 atm, 4 atm, 4.5 atm, 5 atm, 5.5 atm, 6 atm, 6.5 atm, 7 atm, 7.5 atm, 8 atm, 8.5 atm, 9 atm, 9.5 atm, 10 atm, 10.5 atm, 11 atm, 11.5 atm, 12 atm, and so on; or 1.1 bar, 1.5 bar, 2 bar, 2.5 bar, 3 bar, 3.5 bar, 4 bar, 4.5 bar, 5 bar, 5.5 bar, 6 bar, 6.5 bar, 7 bar, 7.5 bar, 8 bar, 8.5 bar, 9 bar, 9.5 bar, 10 bar, 10.5 bar, 11 bar, 11.5 bar, 12 bar, or any intermediate value, or any value greater than the foregoing. Where an ambient air pressure is not provided for comparison in a description herein, the ambient air pressure is intended to be standard atmospheric pressure on Earth at sea level.

The term "pressure cycle" used herein refers to a series of changes in pressure over a period of time. In one embodiment, a pressure cycle comprises a target pressure, that is, the pressure that is to be reached within a given time period. For example, during a pressure cycle, a desired pressure in a chamber starts from being in equilibrium with ambient air pressure, changes to the target pressure, and returns to ambient air pressure. Accordingly, a chamber used in the invention can start a pressure cycle by increasing pressure above atmospheric air and end a pressure cycle by equilibrating with atmospheric air.

In various embodiments of the invention, the start pressure and end pressure may be different, and may each be different from the ambient air pressure. For example, a pulse of positive air pressure is a single pressure cycle. A pressure cycle may in certain embodiments comprise multiple target pressures, e.g., a first target pressure, a second target pressure, a third target pressure, and so on. Thus, different pressure cycles may each have a different start pressure and an end pressure, and any number of discrete intermediate target pressures or a continuous transition from a start pressure to an end pressure.

In the methods of the invention, a plurality of different pressure cycles can be applied and each can be applied one or more times, such as but not limited to two, three, four, five, six, seven, eight, nine, or ten times. Accordingly, in a method of the invention or even in a pressure cycle, the variation of pressure over time can be expressed by a graph or a waveform, such as a sine wave, a square wave, a triangle wave, or a sawtooth wave, or any waveform that approximates one of the foregoing.

In various embodiments of the invention, any specifications of the fluid pressure in terms of duration or extent refer to the overall duration of the pressure cycle and the peak value of the pressure applied to the whole and intact plant, or the plurality of whole plants, or a part of the whole and intact plant. For example, a reference to a pressure cycle comprising treating a whole plant or a plant part with a pressure of at least 4.5 bar for 0.5 seconds, means that the overall duration of the pressure applied to the plant is 0.5 seconds, which may include a period of increasing pressure above atmospheric air and of ending the pressure cycle by equilibrating with atmospheric air, with a peak value of 4.5 bar.

Preferably, a pressure cycle of the invention comprises a target pressure that is a positive pressure. In certain embodiments, the method of the invention does not comprise a target pressure that is a negative pressure. In other embodiments, the methods of the invention comprise a first target pressure that is a positive pressure, as well as a second target pressure that is a negative pressure. In other embodiments, the methods of the invention comprise a first target pressure that is a negative pressure, as well as a second target pressure that is a positive pressure. An optional rest period can be included in the method of the invention between pressure cycles.

Such a rest period may last for about 0.01, 0.05, 0, 1, 0.2, 0.3, 0.4, 0, 5, 1, 1.5, 2, 2.5, 3, 3.5, 4, 4.5, or 5 and up to 10 or more seconds.

In certain embodiments, *Agrobacterium* cells comprising the expression construct are infiltrated into a whole plant, or a plurality of whole plants, particularly a whole and intact plant or a part of a whole and intact plan, including a plant organ or plant tissue in planta. In one embodiment, the infiltration is carried our in the presence of a surfactant, including anionic, cationic, non-ionic, and zwitterionic surfactants.

Non-limiting examples of a surfactant that can be used are Triton X-100 or Silwet L-77, a strong surfactant that shows relatively low toxicity to plants.

After incubating the plant or plant tissue under suitable conditions that allow the expression construct to express the peptide or protein of interest in a plurality of plant cells, the protein can be detected and quantified in the plant or plant part such as the plant organ or plant tissue or in the cells thereof. After harvesting, peptide or protein isolation may be performed using methods routine in the art. For example, at least a portion of the biomass may be homogenized, and recombinant peptide or protein extracted and further purified. Extraction may comprise soaking or immersing the homogenate in a suitable solvent. Purification methods include, but are not limited to, immunoaffinity purification and purification procedures based on the specific size of a peptide, protein or protein complex, electrophoretic mobility, biological activity, and/or net charge of the peptide or protein to be isolated, or based on the presence of a tag molecule in the protein. Characterization of the isolated peptide or protein can be conducted by immunoassay or by other methods known in the art. For example, peptides or proteins can be analyzed on SDS-PAGE gels by Western blotting, or by Coomassie blue staining when the peptide or protein is substantially purified.

In another embodiment of the invention, systems are provided to treat intact whole plants, particularly whole and intact plants or a plant parts such as plant organs or plant tissues that have been contacted with *Agrobacterium* cells upon application of positive fluid pressure. The systems of the invention comprise a chamber for receiving a whole plant, particularly a whole and intact plant or a plant part such as a plant organ or plant tissue, or a plurality of such whole plants or plant parts, and a means for delivering positive fluid pressure. The chamber can be made of any materials known in the art that maintains a definite shape for the purpose of the invention and is not permeable to fluids used in the invention. The chamber comprises a plurality of inlets and outlets, including at least one opening through which a whole plant or plant part such as a plant tissue can be received and retrieved, and the pressure in the chamber is regulated. In certain embodiments, the chamber comprises an opening and a cover adapted for a sealing engagement with the chamber to close the chamber, means forming a valve opening through the side of the chamber or the cover, and a fastening means for releasably maintaining the chamber and the cover in the sealing engagement to a locking position; and at least one flexible valve means, mounted with respect to the valve opening, for providing a fluid path between the interior and exterior of the chamber.

The systems can optionally provide a means whereby a plurality of whole plants or plant parts are contacted with *Agrobacterium* cells. Preferably, the contacting of the whole plants or plant parts with the *Agrobacterium* cells is performed in the chamber where the positive pressure is delivered. Positive fluid pressure can be delivered by any means known in the art.

In one embodiment, the invention provides that a whole and intact plant is positioned upside down inside a chamber and its leaves are wholly immersed in a liquid comprising *Agrobacterium* cells. The chamber is connected to a source of compressed air through a pressure reducer via an inlet valve. The chamber also comprises a release valve installed on one wall, preferably the lid of the chamber. The pressure reducer and the inlet valve are used to regulate the pressure in the chamber, such that one or more of the target pressure(s) can be attained in the chamber. For example, to initiate delivery of a positive pressure, the chamber is closed, the inlet valve is switched to off and the pressure reducer is set to a target pressure. After the plant is immersed in the liquid, the inlet valve is opened for a first period of time sufficient for the chamber to reach the target pressure and a second period of time when the target pressure is maintained in the chamber. After the periods of time have elapsed, the inlet valve is closed, and the release valve is opened allowing the chamber to return to ambient air pressure.

In another embodiment, the invention provides that a whole and intact plant is positioned inside a chamber that comprises a plurality of nozzles and a release valve on the sides of the chamber. The nozzles are connected to a common manifold which in turn is connected via a first inlet valve to a reservoir of a liquid comprising *Agrobacterium* cells. A source of compressed air is connected to the nozzles though a pressure reducer and a second pressure valve. The pressure reducer is used to set the target pressure that is to be attained in the chamber. For example, to initiate delivery of a positive pressure, the chamber is closed, the inlet valve, the pressure valve and the release value are all closed and the pressure reducer is set to a target pressure. Then, the inlet valve and the pressure valve are opened coordinately such that the liquid comprising the bacteria is atomized or aerosolized by the compressed air, and sprayed through the nozzles onto the plant inside the chamber. The inlet valve and pressure valve, or the pressure valve are opened for a first period of time sufficient for the chamber to reach the target pressure and a second period of time when the target pressure is maintained in the chamber. After the periods of time have elapsed, the inlet valve and/or the pressure valve are closed, and the release valve is opened allowing the chamber to return to ambient air pressure.

In other embodiments of the invention, it is contemplated that liquid fluid pressure (or hydraulic pressure) is applied to an enclosed volume of infiltration medium in which a whole and intact plant or a part of a whole and intact plant is submerged. Liquid fluid pressure can be supplied by any conventional means, such as but not limited to hydraulic pumps including gear pump, vane pump, and piston pump.

In addition to the above equipment, the systems of the invention may further comprise various other equipment, such as valves (e.g., relief valves, check valves, manual valves, actuated valves, needle valves, and the like, as well as combinations comprising at least one of the foregoing valves), filters (e.g., bacterial filters, particle filters, and the like as well as combinations thereof), sensors (e.g., pressure, temperature, flow, humidity, conductivity, gas mixture, liquid level, and the like, as well as combinations comprising at least one of the foregoing sensors), controls for temperature (such as, heaters, heat exchangers, coolers, dryers, and the like), controls for pressure (such as, compressors, and the like), flow controls (such as, pumps, fans, blowers, and the like), as well as combinations comprising at least one of the foregoing controls, and conduits (e.g., fluid conduits, electrical conduits, and the like), as well as combinations comprising at least one of the foregoing conduits.

In addition to the above equipment, the systems of the invention can optionally further comprise means for transporting a plurality of whole plants or plant parts such as plant organs or plant tissues from a location to the chamber, means for facilitating the contact of a plurality of whole plants or plant tissues with *Agrobacterium* cells, means for receiving a plurality of whole plants or plant tissues in the chamber, means for positioning and repositioning the plurality of whole plants or plant parts such as plant organs or plant tissues in the chamber, means for retrieving the plurality of whole plants or plant parts from the chamber. Preferably, one or more of the foregoing means are automated electro-mechanical systems, and include but are not limited to motorized transport systems, factory automation systems, security systems, process control systems, data communication systems, data storage systems and computing systems.

In one embodiment of the invention, the chamber comprises means for receiving and positioning a plurality of whole and intact plants within the chamber such that the entire plant comes into contact with the infiltration medium containing the *Argobacterium* cells. In particular, the plurality of plants is positioned such that the entire plant body including its aerial and underground parts is submerged in the infiltration medium containing the *Argobacterium* cells. In this configuration, the entire plant including the aerial parts as well as the underground parts of the plant comes into contact with the infiltration medium containing the *Agrobacterium* cells. The submerged plants are subjected to one or more pressure cycle(s), wherein at least one of the pressure cycle(s) comprises an increase in pressure relative to atmospheric pressure and, in a specific embodiment, the pressure is maintained for a period of between 0.5 seconds and 60 seconds. During one or more pressure cycle(s), the chamber is closed and sealed, preferably with no or negligible air within it, such that when the pressure is applied onto the enclosed infiltration medium, the chamber becomes pressurized due to resistance from the walls of the chamber and a substantially uniform pressure is transmitted throughout the chamber containing the submerged plants. In this configuration, the pressure acting on the submerged plants is substantially the same as that applied to the system.

In another embodiment of the invention, the chamber comprises means for receiving and positioning a plurality of whole and intact plants within the chamber such that only part of the plant comes into contact with the infiltration medium containing the *Argobacterium* cells. In particular, the plurality of plants is positioned such that all or part of the aerial parts of the plant are submerged in the infiltration medium containing the *Argobacterium* cells, while the underground parts of the plant, particularly the roots of the plant, are not submerged in the infiltration medium. In this configuration, the entire plant including the aerial parts as well as the underground parts of the plant are subjected to one or more pressure cycle(s), wherein at least one of the pressure cycle(s) comprises an increase in pressure relative to atmospheric pressure and, in a specific embodiment, the pressure is maintained for a period of between 0.5 seconds and 60 seconds.

FIG. 5 shows an example of such embodiment of the invention. The system 10 comprises a chamber 11 having a lid 12. With the lid 12 the chamber 11 can be sealingly closed. As shown in FIG. 5, in this example whole and intact plants 13 are provided upside down inside a chamber with the aerial parts of the plant being wholly immersed in a liquid. The system 10 also comprises a liquid tank 14 which is connected with the chamber through conduit 15. The liquid tank 14 comprises a plunger rod 16 connected with piston 17. When the piston 17 is moved downwards, liquid from the liquid tank 14 will be pressed into chamber 11 via inlet 19 through conduit 15. The liquid level and also the pressure in the chamber 11 is raised so that the leaves of the plants are immersed and subjected to a pressure which is relative to atmospheric pressure.

In yet another embodiment of the invention, the plurality of plants is positioned in the chamber such that all or part of the aerial parts of the plant are submerged in the infiltration medium containing the *Argobacterium* cells and are subjected to one or more pressure cycle(s), wherein at least one of the pressure cycle(s) comprises an increase in pressure relative to atmospheric pressure and, in a specific embodiment, the pressure is maintained for a period of between 0.5 seconds and 60 seconds. In this configuration, the underground parts of the plant, particularly the plant root, are positioned outside of the chamber such that they are not submerged in the infiltration medium containing the *Agrobacterium* cells and not subjected to the pressure applied during the one or more pressure cycle(s). During one or more pressure cycle(s), the chamber is closed and sealed, preferably with no or negligible air within it, such that when the pressure is applied to the enclosed infiltration medium, the chamber becomes pressurized due to resistance from the walls of the chamber and substantially uniform pressure is transmitted throughout the chamber containing the submerged aerial parts of the plants. In this configuration, the pressure acting on the submerged plants is substantially the same as that applied to the system.

To accommodate aerial parts of whole and intact plant(s) inside a chamber while the underground parts are positioned outside the chamber, one side, typically the top, of the chamber may comprise one or more openings to allow passage of aerial parts of the plants during insertion or removal. The dimensions of an opening are variable due to the presence of parts of the whole and intact plant in the opening. The opening is lined with elastic seals such that the opening can be closed despite the variable dimensions of the opening. The elasticity of the seals may help to protect the plant parts from mechanical damage. Typically, whole intact plants are positioned such that the seal is formed around the main stems due to the elasticity of the seals. The elastic seals can be configured to oppose and slide towards each other to close the opening effectively forming a temporarily airtight or waterproof junction. During a pressure cycle, the chamber can be pressurized temporarily while the infiltration medium and aerial parts of the plants are enclosed by the elastic seals.

An example of such embodiment is shown in FIG. 6. FIG. 6 is a schematic cross sectional view of a chamber 20. Chamber 20 has two wall portions 21, 22 that are connected with each other by means of a hinge 23. The left drawing in FIG. 6 shows the chamber 20 in its open state. At the free ends of the two wall portions 21, 22, inflatable seals 24 are provided. The right drawing of FIG. 6 shows the chamber 20 in its closed state with the two seals 24 being inflated so that the chamber is tightly sealed.

FIG. 7 shows a perspective schematic view of a chamber 26. The chamber 26 shown in the left drawing is in its open state with the two inflatable seals 24 being spaced from each other. Each seal is provided at the edge of a lid portion 25. Lid portions 25 are moveable towards each other and away from each other, for example in a sliding manner. Once the plant is inserted partly (see top right drawing in FIG. 7), the two lid portions 25 are closed around the stem of the plant, and the seals 24 are inflated in order to tightly seal the chamber 26.

It is understood by the skilled person that the shown arrangement with moveable lid portions and longitudinal seals 24 is just an exemplary embodiment and other configurations are encompassed by the invention. For example, instead of having a cylindrical or tubular form, the chamber 26 may have a spherical form with a circular opening for receiving part of the plant. Along the edge of the circular opening, a single annular seal may be provided that is inflatable to such extent that it closes the entire opening of the chamber around the stem of the plant such as to provide airtight or waterproof seal.

In a particular embodiment, the invention provides elastic pneumatic or hydraulic seals, wherein the seals each comprise a cavity in which are introduced compressed air or an inert gas or a hydraulic fluid under an inflation pressure. The inflation pressure causes the otherwise deflated seal to expand flexibly into the gaps that exist between the seal and a part of a whole intact plant, effectively forming a temporarily airtight or waterproof junction. In one particular configuration, at least two opposing seals line an opening in which are positioned the main stem of one or more whole intact plants. Upon inflation, the opposing seals expand into the space between them, until they push against each other and trap the main stem(s) of the plants between them to form a temporarily airtight or waterproof junction. Once the seal inflation pressure is removed, the seal returns to its deflated position, effectively relieving the pressure inside the chamber. It is contemplated that, in one embodiment, the application of inflation pressure to the elastic seals and application of hydraulic pressure to the infiltration medium in the chamber can be sequenced. Preferably, the application of inflation pressure to the elastic seals is in advance of the application of hydraulic pressure such that a junction is formed before the chamber becomes pressurized.

Compressed air is commonly utilized as the inflation medium while in some applications hydraulic (liquid) means may be applied. Inflatable seals offer versatile configurations in three different planes: radially in, radially out, and axially. Seals in the form of trips can form closed ends, mitered ends, and continuous loops. Pneumatic seals or hydraulic seals may be made of variety of elastomers including silicone, Butadiene Styrene (SBR), Chloroprene (Neoprene), Ethylene propylene (EPDM) and Fluorinated Hydrocarbon (Viton®).

Those skilled in the art will recognize that the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electromagnetically actuated devices, or any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs.

In various embodiments, cells of *Agrobacterium* harboring expression constructs with a gene or genes of interest, particularly a heterologous gene or genes of interest, are used to deliver the gene(s) to a whole and intact plan or a plant part such as a plant organ or plant tissue, for transient expression in the cells and/or extracellular spaces of the plant or plant parts. Generally, a suitable expression construct comprises: at least one T-DNA border sequence, an expression regulatory sequence (e.g., a promoter which may be inducible or constitutive, a promoter whose activity is tissue-specific or tissue-biased), and a gene of interest operably linked to the expression regulatory sequence. In certain embodiments, the expression construct further comprises a selectable marker gene under control of a suitable promoter and further expression regulatory sequences. In certain embodiments, an expression construct is part of a vector comprising one or more origins of replication, at least one origin of replication suitable for replicating the vector comprising the expression construct in *Agrobacterium* species.

The *Agrobacterium* species that can be used in the invention include but is not limited to *Agrobacterium tumefaciens*, *Agrobacterium rhizogenes* *Agrobacterium radiobacter*, *Agrobacterium rubi*, *Argobacterium vitis*, but particularly *Agrobacterium tumefaciens* and *Agrobacterium rhizogenes*. In one embodiment, at least one *Agrobacterium* strain comprises *Agrobacterium tumefaciens*. The *Agrobacterium* species used can be a wild type (e.g., virulent) or a disarmed strain. Suitable strains of *Agrobacterium* include wild type strains (e.g., such as *Agrobacterium tumefaciens*) or strains in which one or more genes is mutated to increase transformation efficiency, e.g., such as *Agrobacterium* strains wherein the vir gene expression and/or induction thereof is altered due to the presence of mutant or chimeric virA or virG genes (e.g. Chen and Winans, 1991, J. Bacteriol. 173: 1139-1144; and Scheeren-Groot et al., 1994, J. Bacteriol. 176:6418-6246), *Agrobacterium* strains comprising an extra virG gene copies, such as the super virG gene derived from pTiBo542, preferably linked to a multiple-copy plasmid, as described in U.S. Pat. No. 6,483,013, for example. Other suitable strains include, but are not limited to: *A. tumefaciens* C58C1 (Van Larebeke et al., Nature 252: 169-170 (1974)), A136 (Watson et al., J. Bacteriol 123: 255-264 (1975)); LBA401 1 (Klapwijk et al., J. Bacteriol 141: 128-136 (1980)), LBA4404 (Hoekema et al., Nature 303: 179-180 (1983)); EHA101 (Hood et al., J. Bac. 168: 1291-1301 (1986)); EHA105 (Hood et al., Trans Res. 2: 208-218 (1993)); AGL1 (Lazo et al., Bio/Technology 2: 963-967 (1991)); A281 (Hood et al., supra (1986)).

Multiple *Agrobacterium* strains, each expressing different genes can be used to produce the individual proteins or a heteromultimeric protein, or to enhance the yield of a peptide or protein of interest. A non-limiting example of a different gene that can be expressed is a gene that encodes a silencing suppressor of viral origin. Alternatively, or additionally, a single *Agrobacterium* strain may comprise a plurality of sequences comprising different genes of interests, particularly heterologous genes of interest. The different genes may be comprised within a single nucleic acid molecule (e.g., a single vector) or may be provided in different vectors.

The methods of the invention can be used for *Agrobacterium* infiltration and transient expression of many species of plants, including but not limited to: tobacco (*Nicotiana* species), lettuce, alfalfa, mung bean, spinach, dandelion, radicchio, arugula, endive, escarole, chicory, artichoke, maize, potato, rice, soybean, cotton, small grain cereals, wheat, barley, *Sorghum*, sugar beet, canola, *Crucifera* (e.g., *Brassica*, *Arabidopsis*) duckweed, and tomato.

Suitable plant organ or tissue generally can be any part of the plant. In one preferred aspect, plant tissue is leaf tissue. In one aspect, the plant tissue is leaf tissue from a plant comprising leaves of at least about 7-8 cm in at least one dimension.

In various embodiments, a plant species, variety or even a plant organ is selected whose cells comprise undetectable or low levels of proteases which digest heterologous proteins, e.g., less than about 5%, less than about 1%, less than about 0.1% of heterologous proteins expressed in the plant are digested during the period of time from introduction of nucleic acids expressing the heterologous protein to at least about the time when the protein is isolated from the plant tissue. Protease levels can be assayed for using methods routine in the art, including Western blot analysis of heterologous protein expression.

Exemplary species of the *Nicotiana* genus include, but are not limited to: *Nicotiana africana*, *Nicotiana amplexicaulis*, *Nicotiana arentsii*, *Nicotiana benthamiana*, *Nicotiana bigelovii*, *Nicotiana corymbosa*, *Nicotiana debneyi*, *Nicotiana excelsior*, *Nicotiana exigua*, *Nicotiana glutinosa*, *Nicotiana goodspeedii*, *Nicotiana gossei*, *Nicotiana hesperis*, *Nicotiana ingulba*, *Nicotiana knightiana*, *Nicotiana maritima*, *Nicotiana megalosiphon*, *Nicotiana miersii*, *Nicotiana nesophila*, *Nicotiana noctiflora*, *Nicotiana nudicaulis*, *Nicotiana otophora*, *Nicotiana palmeri*, *Nicotiana paniculata*, *Nicotiana petunioides*, *Nicotiana plumbaginifolia*, *Nicotiana repanda*, *Nicotiana rosulata*, *Nicotiana rotundifolia*, *Nicotiana rustica*, *Nicotiana setchelli*, *Nicotiana stocktonii*, *Nicotiana eastii*, *Nicotiana suaveolens* or *Nicotiana trigonophylla*. Desirably the first tobacco plant is *Nicotiana amplexicaulis*, *Nicotiana benthamiana*, *Nicotiana bigelovii*, *Nicotiana debneyi*, *Nicotiana excelsior*, *Nicotiana glutinosa*, *Nicotiana goodspeedii*, *Nicotiana gossei*, *Nicotiana hesperis*, *Nicotiana knightiana*, *Nicotiana maritima*, *Nicotiana*

*megalosiphon, Nicotiana nudicaulis, Nicotiana paniculata, Nicotiana plumbaginifolia, Nicotiana repanda, Nicotiana rustica, Nicotiana suaveolens* or *Nicotiana trigonophylla.*

Exemplary varieties of *Nicotiana tabacum* include commercial varieties such as DAC Mata Fina, PO2, BY-64, AS44, RG17, RG8, HBO4P, Basma Xanthi BX 2A, Coker 319, Hicks, McNair, 944 (MN 944), Burley 21, K149, Yaka JB 125/3, Kasturi Mawar, NC 297, Coker 371 Gold, Wislica, Simmaba, Turkish Samsun, AA37-1, B13P, F4 from the cross BU21×Hoja Parado, line 97, Samsun, PO1BU 64, CC 101, CC 200, CC 27, CC 301, CC 400, CC 500, CC 600, CC 700, CC 800, CC 900, Coker 176, Coker 319, Coker 371 Gold, Coker 48, CU 263, DF911, Galpao tobacco, GL 26H, GL 350, GL 737, GL 939, GL 973, HB 04P, K 149, K 326, K 346, K 358, K 394, K 399, K 730, KT 200, KY 10, KY 14, KY 160, KY 17, KY 171, KY 907, KY 160, Little Crittenden, McNair 373, McNair 944, msKY 14.times.L8, Narrow Leaf Madole, NC 100, NC 102, NC 2000, NC 291, NC 297, NC 299, NC 3, NC 4, NC 5, NC 6, NC 606, NC 71, NC 72, NC 810, NC BH 129, OXFORD 207, 'Perique' tobacco, PVH03, PVH09, PVH19, PVH50, PVH51, R 610, R 630, R 7-11, R 7-12, RG 17, RG 81, RG H4, RG H51, RGH 4, RGH 51, RS 1410, SP 168, SP 172, SP 179, SP 210, SP 220, SP G-28, SP G-70, SP H20, SP NF3, TN 86, TN 90, TN 97, TN D94, TN D950, TR (Tom Rosson) Madole, VA 309, VA 309, or VA 359.

Tobacco plants of any stage can be used, particularly the tobacco plants are at stage 6, 7, 8, 9, 10, 11, 12, 13, 14, or 15. In a specific embodiment of the invention, plants at stage 8, 9 or 10 are used, wherein the plants have an average height of between about 6.5 cm and about 16.5 cm. At stage 10, the plants are 5-6 week-old and have a height of around 15 cm, with well expanded leaves and maximum one flower open.

An alternative system that identifies key growth stages in tobacco ranging from a scale of 1-9 is disclosed in the CORESTA Guide N° 7 of February 2009, "A Scale For Coding Growth Stages In Tobacco Crops", Task Force Growth Stages and Identification Keys for Tobacco, pp. 1-15, Centre de Co-operation pour les Recherches Scientifiques au Tabac. (http://www.coresta.org/Guides/Guide-No7-Growth-Stages_Feb09.pdf). According to the CORESTA system, plants in growth stages 2-8 may be used, but particularly plants in growth stages 3-5.

A tobacco plant with a large leaf surface area is preferred. It is a particular advantage of the invention that already grown plants can be used in the methods of the invention or used as a source of plant tissues.

The invention provides systems and methods that make it possible to take advantage of protein production in grown, commercially available plants, tobacco in particular, and provides a novel solution to the problem of procuring the necessary amounts of recombinant heterologous peptides or proteins for therapeutic or prophylactic uses in a short period of time.

In one aspect of the invention, the method comprises introducing an expression construct comprising a sequence encoding a heterologous peptide or protein of interest or biologically active fragment thereof into a whole plant or plant part such as a plant tissue and transiently expressing the protein in the plant or plant part. The encoding sequence is operably linked to an expression control sequence capable of driving transcription of the encoding sequence in the cells and/or in the extracellular spaces of the plant or plant part. Preferably, the expression construct comprises at least one T border sequence from T-DNA of a large tumor-inducing ("Ti") plasmid. Also, preferably, the expression construct is comprised within a vector capable of replicating in at least the cells of an *Agrobacterium* species, such as *Agrobacterium tumefaciens*. In one aspect, the whole plant or plant part comprises leaf tissue from an already grown plant. Preferably, the plant comprises relatively large leaves (e.g., greater than about 7-8 cm in at least one dimension), e.g., *Nicotiana tabacum*).

The expression construct may be part of an expression vector and can include additional desirable sequences such as bacterial origins of replication (*Agrobacterium* and/or *E. coli* origins of replication), reporter genes that function in bacteria such as *Agrobacterium* and/or plant cells (e.g., GUS, GFP, EGFP, BFP, beta-galactosidase and modified forms thereof) and selectable marker genes (e.g., antibiotic resistance genes, and the like). To this end, the foreign DNA used in the method of this invention may also comprise a marker gene, the expression of which allows the separation of transformed cells from non-transformed cells during initial cloning stages. Such a marker gene generally encodes a protein which allows one to phenotypically distinguish transformed cells from untransformed cells. However, it is an advantage of the transient protein production methods according to the invention that marker genes are not required to isolate heterologous peptides or proteins from plant tissues into which expression constructs/vectors are introduced.

The expression constructs may further be complemented with a silencing suppressor, particularly a viral silencing suppressors, including, without being limited to, the p25 protein of PVX, the P1-HcPro protein of tobacco etch virus, and the p19 protein of tomato bushy stunt virus.

As used herein, level of transient expression refers to the capacity to express of at least about 250 microgram, at least about 500 microgram, at least about 750 microgram, at least about 1 mg, at least about 2 mg, at least about 3 mg, at least about 4 mg, at least about 5 mg, at least about 10 mg, at least about 15 mg, at least about 25 mg, at least about 50 mg, at least about 75 mg, at least about 100 mg, at least about 150 mg, at least about 200 mg, at least about 500 mg, at least about 1000 mg, at least about 1.5 g, at least about 2 g, at least about 2.5 g, at least about 5 g, at least about 7.5 g, at least about 10 g, at least about 15 g, or at least about 20 g per kg of plant tissue mass. As used herein, "transient" refers to a period of time that is long enough to permit isolation of protein from a suitable plant tissue. Preferably, protein expression is at suitably high levels within at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, or at least about 15 days after introduction of the expression construct into plant tissue. In one aspect, suitably high levels are obtained within 3-7 or 5-10 days and more preferably within 3-5 or 5-7 days, after introduction of an expression construct into the plant tissue.

Recombinant proteins produced by methods of the invention may be used as pharmaceuticals, and can be expressed for their utility as nutraceuticals and cosmeceuticals, since these products are used for direct ingestion, injection or application (e.g., topical administration) to humans. Recombinant protein also may be expressed which are useful in the production of similarly regulated veterinarian products. Exemplary proteins which may be produced, include, but are not limited to: growth factors, receptors, ligands, signaling molecules; kinases, enzymes, hormones, tumor suppressors, blood clotting proteins, cell cycle proteins, metabolic proteins, neuronal proteins, cardiac proteins, proteins deficient in specific disease states, antibodies, antigens, proteins that provide resistance to diseases, antimicrobial proteins, interferons, and cytokines.

In one aspect, antigen encoding sequences includes sequences for inducing protective immune responses (e.g., as in a vaccine formulation). Such suitable antigens include but are not limited to microbial antigens (including viral antigens, bacterial antigens, fungal antigens, parasite antigens, and the like); antigens from multicellular organisms (such as multicellular parasites); allergens; and antigens associated with human or animal pathologies (e.g., such as cancer, autoimmune diseases, and the like). In one preferred aspect, viral antigens include, but are not limited to: HIV antigens; antigens for conferring protective immune responses to influenza; rotavirus antigens; anthrax antigens; rabies antigens; and the like. Vaccine antigens can be encoded as multivalent peptides or polypeptides, e.g., comprising different or the same antigenic encoding sequences repeated in an expression construct, and optionally separated by one or more linker sequences.

Methods of the invention can also be used to express one or more genes to reproduce enzymatic pathways for chemical synthesis or for industrial processes.

The present invention is further described by reference to the following non-limiting figures, tables and examples.

BRIEF DESCRIPTION OF FIGURES AND TABLES

FIG. 1 shows a schematic view of a set up of a overpressure system comprising a pressure chamber. V1, V2, V3: valves; M1: manometer; S1: silencer.

Figure 1:
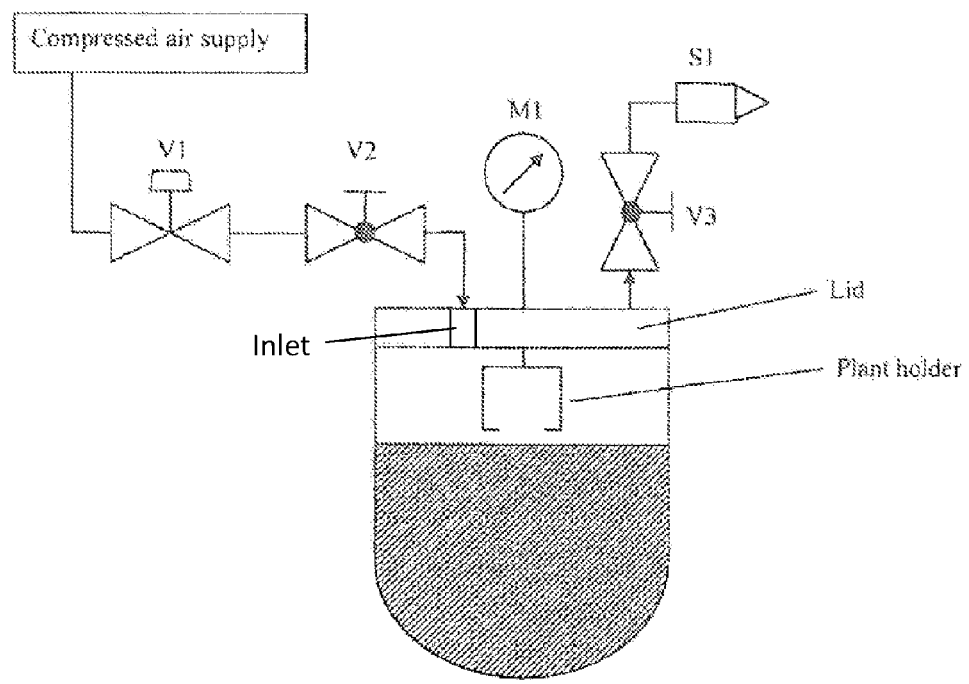

Table 1 shows experimental information on composition A91 (AGL1 strain carrying gene for the fluorescent protein TurboGFP) and A17 (AGL1 strain carrying the gene for p19 suppressor of silencing) used within the preparation of the *Agrobacterium* inoculum.

Table 2 shows experimental information on composition A91 (AGL1 strain carrying gene for the fluorescent protein TurboGFP) and A17 (AGL1 strain carrying the gene for p19 suppressor of silencing) used within the preparation of the *Agrobacterium* inoculum.

Table 3 shows six different conditions with parameters used within infiltration experiment.

Table 4 shows nine different conditions with parameters used within a further infiltration experiment.

Table 5 shows standard dilutions of TurboGFP control protein (rTurbo GFP, Evrogen #FP552) in plant extract (mock extract from N.b. leaf sample infiltrated with A17 only that does not express TurboGFP).

Table 6 shows analysis of differences between the conditions based on GFP concentration expressed in µg GFP per g frozen weight with a confidence interval of 95%.

Table 7 shows analysis of the differences between the conditions based on GFP concentration expressed in % TSP ("Total Soluble Protein") with a confidence interval of 95%.

Table 8 shows analysis of the differences between the conditions based on µg GFP/g frozen weight of infiltrated leaves with a confidence interval of 95%.

Table 9 shows analysis of the differences between the conditions based on mg GFP per plant with a confidence interval of 95%.

Table 10 shows analysis of the differences between the conditions based on GFP concentration in percentage of TSP ("Total Soluble Protein") concentration with a confidence interval of 95%.

Table 11 shows ANOVA comparing overpressure in optimal conditions and reference.

Table 12 shows means with individual 95% confidence intervals for optimal conditions and reference.

The foregoing description will be more fully understood with the reference to the following Examples. Such Examples are, however, exemplary methods of practicing the present invention and are not intended to limit the scope of the invention.

EXAMPLES

Part A

Evaluation of Efficiency of Agro-Infiltration by Positive Pressure as Compared to Vacuum for the Transfection of *N. Benthamiana*

Example 1

Overall Set Up

Plants were infiltrated with a bacterial suspension consisting of a mixture of A91 (AGL1 *Agrobacterium* strain carrying the gene for the fluorescent protein TurboGFP) and A17 (AGL1 *Agrobacterium* strain carrying the gene for the p19 suppressor of silencing).

TurboGFP is an improved variant of the green fluorescent protein CopGFP cloned from copepod *Pontellina plumata* (Arthropoda; Crustacea; Maxillopoda; Copepoda) [Shagin D A, et al., GFP-like proteins as ubiquitous metazoan superfamily: evolution of functional features and structural complexity. Mol Biol Evol. 2004; 21 (5):841-50]. It possesses bright green fluorescence (excitation/emission max=482/502 nm) that is visible earlier than fluorescence of other green fluorescent proteins. Turbo GFP is available from Evrogen (Evrogen Joint Stock Company; Miklukho-Maklaya str, 16/10, 117997, Moscow, Russia)

Expression of TurboGFP in the infiltrated plants was
1) regularly monitored by imaging of the whole plants or detached infiltrated leaves under blue light between two days post infiltration to the day of harvest and
2) quantified after extraction in a microplate fluorescence reader.

1.1 Vacuum Infiltration:

Vacuum infiltration was performed with a Labconco vacuum chamber with internal dimensions of 30×30×30 cm modified by addition of a vacuum relief valve (5 mm diameter) and a V-710 Büchi pump (3.8 m$^3$/hour)+V-855 regulator. The vacuum parameters applied were as follows:
  pressure decrease from atmospheric to 50 mbar absolute in 3 minutes,
  1 minute holding time at 50 mbar,
  fast relief in about 3 seconds.

For this experiment, plants were infiltrated one at a time by immersion of the aerial part in a 1 or 2 L beaker filled with the bacterial suspension.

1.2 Overpressure:

The overpressure setup is shown in FIG. 1. Plants were placed upside down inside one pressure chamber (Volume of about 10 liters) through an ad-hoc holder connected to the top lid. The holder position was adjusted to minimize the clearance between the liquid surface and the holder. Once the lid is closed, the following sequence was carried out to treat the plants and *Agrobacterium* with positive pressure:

1. With the manual ball valves V2 and V3 closed the regulating valve V1 was set to the desired compressed air pressure.
2. V2 was open for 10 s and the pressure reached inside the tank was monitored through the manometer M1.
3. V2 was closed and the tank brought back to atmospheric pressure by opening V3 and venting the system through the silencer S1.
4. The lid was opened, the plant removed from the holder.

Example 2

Preparation of the *Agrobacterium* Inoculum

A 6× concentrated inoculum consisting of a mixture of A91 (AGL1 strain carrying the gene for the fluorescent protein TurboGFP) and A17 (AGL1 strain carrying the gene for the p19 suppressor of silencing) was prepared (Table 1 and 2) and stored at 4° C. until the day of infiltration.

TABLE 1

| Composition | A91-A17 |
|---|---|
| Volume | 3.3 L |
| OD600 nm | 1.926 |
| Concentration | 6X |
| To be diluted in xL of infiltration solution | 16.7 L |
| Infiltration solution composition | 5 mM MES, 10 mM MgCl2, pH 5.6 |
| Glycerol 1 | A91.393 09.09.09 JBE |
| Glycerol 2 | A17.1 16.06.09 SRO |
| Final OD600 culture 1 | 3.3 |
| Final OD600 culture 2 | 3.1 |

TABLE 2

| Composition | A91-A17 |
|---|---|
| Volume | 2× 1 L |
| OD600 nm | 2.0 |
| Concentration | 6X |
| To be diluted in xL of infiltration solution | 2X 5 L |
| Infiltration solution composition | 5 mM MES, 10 mM MgCl2, pH 5.6 |
| Glycerol 1 | A91.393 09.09.09 JBE |
| Glycerol 2 | A17.1 24.09.09 SRO |
| Final OD600 culture 1 | A91: 2.27 |
| Final OD600 culture 2 | A17: 2.25 |

The concentrated inoculum was diluted to 1× final concentration in infiltration solution (5 mM MES. 10 mM MgCl2, pH5.6) at room temperature (~20° C.) ~1 hour before the start of the infiltrations. The 1× final concentration corresponds to a final $OD_{600\ nm}$ of 0.3 with a 1:1 ratio of A91 and A17.

For the $2^{nd}$ experiment, a 1% (v/v) Triton X-100 stock solution was prepared in infiltration solution and, when specified, added to the inoculum in the infiltration tank at a 1:100 dilution to reach a final Triton X-100 concentration of 0.01% (v/v).

Example 3

Biomass Production

*Nicotiana benthamiana* accession MIM plants were grown in the greenhouse with 20 h light, 26° C./20° C. day/night temperature and 70%/50% day/night relative humidity. Artificial lightening is turned automatically on between 02h00 to 22h00 when natural fight is under 200 W/m2 (20 hours light) with a 15'000 or 20'000 Lux lighting system giving a PAR of about 100 μmol/m²/s. Plants were grown in rockwool blocks (Grodan Delta Grow Blocks size 6.5). Fert-irrigation by sub-irrigation was applied every 2 days: 25 mm water during 30 minutes. The fertilization was adjusted to an EC of 2.5 mS/cm and a pH of 5.8.

Example 4

Infiltration Parameters

In an infiltration experiment, six different conditions were compared. The parameters used are reported in table 3.

TABLE 3

| Order | Condition | Target pressure [bar] | Holding time [s] | Number of replicates | Plant # |
|---|---|---|---|---|---|
| 1 | Vacuum | 0.05 absolute | 60 | 6 | 1-6 |
| 2 | Overpressure | 1 | 10 | 6 | 7-12 |
| 3 | Overpressure | 2.5 | 10 | 6 | 13-18 |
| 4 | Overpressure | 0.5 | 10 | 6 | 19-24 |
| 5 | Overpressure | 1.5 | 10 | 6 | 25-30 |
| 6 | Overpressure | 2 | 10 | 6 | 31-36 |

In a second infiltration experiment, nine different conditions were compared. The parameters used are reported in table 4.

TABLE 4

| Order | Condition | Target pressure [bar] | Holding time [s] | Number of replicates | Plant # |
|---|---|---|---|---|---|
| 1 | Syringe | unknown | — | 6 | 1-6 |
| 2 | Vacuum | 0.05 absolute | 60 | 6 | 7-12 |
| 3 | Overpressure | 2.5 | 10 | 6 | 13-18 |
| 4 | Overpressure | 1.5 | 10 | 6 | 19-24 |
| 5 | Overpressure | 2.0 | 10 | 6 | 25-30 |
| 6 | Overpressure | 3.5 | 10 | 6 | 31-36 |
| 7 | Overpressure | 3.0 | 10 | 6 | 37-42 |
| 8 | Overpressure + 0.01% Triton | 2.5 | 10 | 6 | 43-48 |
| 9 | Vacuum + 0.01% Triton | 0.05 absolute | 60 | 6 | 49-54 |

Plants were weighted immediately before starting the infiltration sequence. At the end of the infiltration, plants were taken out of the chambers and held upside-down in a "dripping rack". Weight measurements were taken respectively 2 and 10 minutes after the completion of the venting step. In between these two measurements plants were again placed upside-down in the rack, while at the end of the last weighing they were positioned in the recovery area. The difference in weight before and after infiltration may be used as an indicator of the volume of inoculum infiltrated in the plant.

Example 5

Recovery and Incubation Conditions

Following infiltration, plants were placed on greenhouse benches in the S2 compartment until harvesting. Water and fertilizer were administered to plants when needed using a drip irrigation system. The environmental conditions such as fertilization, photoperiod and temperature used during the recovery and incubation phase were the same as used for growing the plants (see above). There was no dark incubation of plants because it has previously been shown that does not affect turboGFP expression.

Example 6

Setup for Fluorescence Imaging

Transient expression of the turbo GFP was monitored by photographing plants under blue light 5 or 6 days following infiltration. A Dark reader lamp (HL32T Hand Lamp, Clare Chemical Research, USA) which emits light within the range of excitation of the turbo GFP (excitation maximum at 482 nm) was used. Photographs were taken in a dark environment with a digital camera equipped with an amber filter provided by the lamp manufacturer.

Example 7

Harvesting

Plants were then placed under blue light and all expanded and infiltrated leaves showing fluorescence were collected. Leaves at the apex of the main and axillary shoots showing fluorescence only at the tip were not harvested. The harvested leaves were first placed under a plastic sheet for fluorescence imaging. They were then placed in a zip-bag and transferred to 4° C. until harvesting was completed. All bags were then brought back to the lab and transferred to minus 80° C. until the leaves were processed for analysis.

Example 8

Fluorescence Quantitation

The content of each bag was ground to a fine powder using the coffee-grinder/dry-ice method so that one sample corresponds to all infiltrated leaves harvested from a single plant fully homogenized. Sub-samples of 1.00 g+/−0.05 g frozen weight of powder were prepared on dry-ice for extraction. Extraction was performed at a ratio of 1 g frozen weight for 3 mL extraction buffer (50 mM Tris base; 100 mM NaCl; EDTA 1 mM; 0.2% Triton X-100; pH 7.5) by two steps of vortexing for 20 seconds followed by centrifugation at 20'000 g for 15 min. Soluble extracts were kept on ice for analysis.

TurboGFP concentration (Ex max: 482 nm/Em. max 502 nm) in the extracts was determined by fluorescence measurement on a Modulus microplate reader (Turner Biosystems) in Fluorescence mode with Blue optical kit (Ex: 490 nm/Em: 510-570 nm). Extracts were diluted 1:100 in extraction buffer and 200 μL were loaded in triplicate on a black 96-well plate. A standard curve was prepared by adding different amounts of TurboGFP control protein (rTurbo GFP, Evrogen #FP552) to a mock-extract diluted 1:100 final in extraction buffer (extract from N.b. leaf sample infiltrated with A17 only and prepared in the same conditions as described for the samples). Fluorescence from the samples diluted 1:100 ranged from 0.4 to 1.3×10'000 units in the first experiment and 1.4 to 2.5×10'000 units in the second experiment with a variation coefficient (CV)<2% between triplicates.

TABLE 5

|  | Turbo GFP conc. in μg/mL | Vol. rTurboGFP at 10 μg/mL | Vol. mock extract diluted 1:50 | Vol. extraction buffer |
|---|---|---|---|---|
| Std 1 | 4.0 | 320 μL | 400 μL | 80 μL |
| Std 2 | 3.0 | 240 μL | 400 μL | 160 μL |
| Std 3 | 2.5 | 200 μL | 400 μL | 200 μL |
| Std 4 | 2.0 | 160 μL | 400 μL | 240 μL |
| Std 5 | 1.5 | 120 μL | 400 μL | 280 μL |
| Std 6 | 1.0 | 80 μL | 400 μL | 320 μL |
| Std 7 | 0.5 | 40 μL | 400 μL | 360 μL |
| Std 8 | 0.25 | 20 μL | 400 μL | 380 μL |
| Std 9 | 0.125 | 10 μL | 400 μL | 390 μL |
| Blank | 0 | 0 μL | 400 μL | 400 μL |

A Standard curve of fluorescence units as a function of TurboGFP concentration. This curve was obtained by reading fluorescence on a Modulus microplate reader (Turner Biosystems) in Fluorescence mode with Blue optical kit from 200 μL of standard dilutions of TurboGFP control protein (rTurbo GFP, Evrogen #FP552) in plant extract (mock extract from N.b. leaf sample infiltrated with A17 only that does not express TurboGFP) prepared as indicated in the table. Each dilution was read in triplicates and the standard error of the mean (SE) calculated (<0.01×10'000 fluorescence units, not represented). This standard curve was used to quantify TurboGFP concentration in soluble extracts prepared from infiltrated plant material expressing TurboGFP.

Example 9

Total Soluble Protein Quantitation

Total soluble protein in the extracts was determined using the Coomassie-Plus Assay reagent from Pierce (#24236) by absorbance measurement on a microplate reader at 595 nm. Extracts were diluted 1:10 or 1:20 in ultrapure water and 10 μL were loaded in triplicate on a flat-bottom microplate. A standard curve was prepared from serial dilutions of Bovine Serum Albumin (BSA) in a concentration range of 100 to 400 μg/mL. Results were considered to be valid when variation coefficient (CV) between triplicates was below 8%.

Results

A first infiltration experiment was performed to compare the efficiency of infiltration by vacuum (50 mbar absolute) with positive pressure values ranging from 0.5 bar to 2.5 bar (Table 3).

Efficiency of infiltration was first assessed by looking at the distribution of the inoculum over the leaf area just after infiltration. When observing the abaxial side of the leaves, infiltrated areas appear as dark green. In plants infiltrated by vacuum, almost 100% of the area of all leaves was uniformly infiltrated. Plants infiltrated using positive pressure ranging from 0.5 to 1.5 bar showed a very patchy distribution of inoculum over the leaf area. Bottom leaves were less infiltrated. Plants infiltrated using positive pressure values ranging from 2.0 to 2.5 bar showed a more uniform distribution of the inoculum although infiltration was not as complete as in plants infiltrated by vacuum.

A second experiment was performed using positive pressures ranging from 1.5 bar to 3.5 bar (table 4) to improve the penetration of the inoculum inside the leaf. The addition of 0.01% Triton X-100 to the inoculum in combination with 2.5 bar overpressure condition was also tested. Addition of detergents has been reported to enhance efficiency of infiltration and *Agrobacterium*-mediated transient expression in several plant systems. Three control conditions were used: plants infiltrated by vacuum at 50 mbar, with or without 0.01% Triton X-100, and by syringe.

In this second experiment, the plants used had reached a more advanced developmental stage (stage 10, average 16.5 cm height compared to only 6.5 cm in the first experiment corresponding to a stage 8) with more expanded leaves. Plants were generally better infiltrated than during the first experiment even at the lowest positive pressure used which was at 1.5 bar. There may be two main reasons to this: 1) for practical reasons, the size of the plants made it easier to ensure that all leaves were fully immersed in the inoculum in the overpressure tank and 2) expanded leaves may have been more efficiently infiltrated because of the structure of the leaf tissues with more void in the intercellular space facilitating the spread of the inoculum. A trend was detected as it was first noticed in the first experiment wherein the higher the overpressure, the more uniform and complete the infiltration. Plants infiltrated with 3.0 or 3.5 bar showed a very uniform distribution of the inoculum that seemed comparable to that of plants infiltrated by vacuum. No clear effect of the use of 0.01% Triton-X100 could be detected at this stage.

The phenotype of the plants during the recovery and incubation phase after infiltration was monitored. At the time of harvest, a slight decrease in chlorophyll content (not quantified) was visible in infiltrated leaves, i.e. a paler green colour, independently of the conditions used for infiltration. No other stress-related signs such as wilting, severe chlorosis or necrosis were observed in any of the infiltration conditions.

Expression of TurboGFP in the plants co-infiltrated with A91 and A17 was regularly monitored during the incubation phase (from 2 days post infiltration to the day of harvest) by placing the plants in a black box under blue light and observing or imaging the fluorescence from the TurboGFP with an amber filter. Leaf areas where GFP is expressed emit green fluorescence. Leaf areas where no or low concentrations of GFP are expressed appear in red due to natural autofluorescence from plant tissues.

For all infiltration conditions, low GFP expression was already visible at 2 days post-infiltration and increased with time in infiltrated leaves whilst at the same time, plants continued to develop and newly expanded leaves at the apex that had not been infiltrated did not show GFP fluorescence and appeared in red. In the first and second experiment (not shown as due to the size of the plants, imaging of whole plants was not technically feasible), clear differences in GFP expression were visible between plants infiltrated in different conditions.

These differences may be observed more easily from images of detached leaves taken on the day of harvest. In the first experiment, a very patchy pattern of GFP fluorescence was observed from leaves of plants infiltrated using the lowest overpressure (0.5 to 1.5 bars) with a very weak fluorescence from bottom leaves. A brighter GFP fluorescence was observed from bottom leaves of plants infiltrated by vacuum than from leaves of plants infiltrated in any of the positive pressure conditions including the highest value of 2.5 bar. In this experiment using small plants (average 6.5 cm height), only a small number of leaves (generally 4-6) per plant showed GFP fluorescence at the time of harvest and were collected for quantitation.

Quantitation was performed after total soluble protein extraction from frozen powder obtained from the leaves collected for each plant. Results and statistical analysis (Tables 6 and 7) clearly show that GFP expression in plants infiltrated by positive pressure was significantly lower than that in plants infiltrated by vacuum even at the highest overpressure used in this experiment (2.5 bar). A general trend also appeared: the higher the overpressure used the higher the GFP expression in infiltrated leaves.

It was already noted that plants used in the second experiment were at a more advanced developmental stage (Stage 10, average 16.5 cm height) and were generally better infiltrated than during the first experiment. This was reflected by the number of leaves effectively expressing TurboGFP and collected for each plant by a higher yield of the TurboGFP per unit of biomass which on average was two times higher than the yield obtained in the first experiment. It is important to note that less material was collected from syringe-infiltrated plants since only expanded leaves could be infiltrated by this method resulting in overall less infiltrated leaves than with the other method. Quantitation data (tables 8 to 10) indicate that TurboGFP expression in plants infiltrated with an overpressure of 3.0 bar was not significantly different from that in plants infiltrated by syringe or vacuum (without Triton). Differences in expression in plants infiltrated with pressure values ranging from 2.0 to 3.0 bars were not statistically significant. However, a significantly lower GFP expression was observed in plants infiltrated with 1.5 bar. Addition of 0.01% Triton X-100 to the inoculum lead to a significant but moderate increase (<15% increase per plant) in TurboGFP accumulation in plants infiltrated by vacuum. The effect of adding 0.01% Triton X-100 in conjunction with a positive pressure at 2.5 bar was not as clear.

TABLE 6

Analysis of the differences between the conditions with a confidence interval of 95%

| Condition | Mean | Groups | | |
|---|---|---|---|---|
| V50 | 435.415 | A | | |
| OP2.5 | 258.117 | | B | |
| OP2.0 | 250.960 | | B | |
| OP1.5 | 230.440 | | B | C |
| OP1.0 | 229.236 | | B | C |
| OP0.5 | 167.226 | | | C |

Grouping of infiltration conditions based on GFP concentration expressed in µg GFP per g frozen weight using each pairs student t test with a confidence interval of 95% (levels not connected by the same letter are significantly different).

TABLE 7

Analysis of the differences between the conditions with a confidence interval of 95%

| Category | LS means | Groups | | |
|---|---|---|---|---|
| V50 | 5.083 | A | | |
| OP2.0 | 3.213 | | B | |
| OP2.5 | 3.106 | | B | |
| OP1.5 | 2.740 | | B | C |
| OP1.0 | 2.571 | | B | C |
| OP0.5 | 2.066 | | | C |

Grouping of infiltration conditions based on GFP concentration expressed in % TSP using each pairs student t test with a confidence interval of 95% (levels not connected by the same letter are significantly different).

TABLE 8

Analysis of the differences between the conditions with a confidence interval of 95%

| Condition | Mean | Groups | | | |
|---|---|---|---|---|---|
| V50 w Triton | 790.751 | A | | | |
| V50 | 723.700 | | B | | |
| Syringe | 649.413 | | | C | |
| OP3.0 | 627.456 | | | C | D |
| OP2.5 w Triton | 606.548 | | | C | D |
| OP2.0 | 601.443 | | | C | D |
| OP3.5 | 580.485 | | | | D |
| OP2.5 | 576.924 | | | | D |
| OP1.5 | 494.170 | | | | | E |

Grouping of infiltration conditions based on microgram GFP/g frozen weight of infiltrated leaves using each pairs student t test with a confidence interval of 95% (levels not connected by the same letter are significantly different).

TABLE 9

Analysis of the differences between the conditions with a confidence interval of 95%

| Condition | Mean | Groups | | | |
|---|---|---|---|---|---|
| V50 w Triton | 18.637 | A | | | |
| V50 | 15.923 | | B | | |
| OP3.0 | 14.760 | | B | C | |
| Syringe | 13.777 | | B | C | |
| OP3.5 | 13.377 | | | C | |
| OP2.0 | 13.093 | | | C | D |
| OP2.5 w Triton | 13.065 | | | C | D |
| OP2.5 | 12.304 | | | C | D |
| OP1.5 | 10.610 | | | | D |

Grouping of infiltration conditions based on mg GFP per plant using each pairs student t test with a confidence interval of 95% (levels not connected by the same letter are significantly different).

TABLE 10

Analysis of the differences between the conditions with a confidence interval of 95%

| Condition | Mean | Groups | | | |
|---|---|---|---|---|---|
| V50 w Triton | 9.668 | A | | | |
| V50 | 8.618 | | B | | |
| Syringe | 8.514 | | B | | |
| OP3.0 | 7.891 | | B | C | |
| OP2.5 w Triton | 7.535 | | | C | D |
| OP2.0 | 7.214 | | | C | D |
| OP2.5 | 6.857 | | | | D |
| OP3.5 | 6.679 | | | | D | E |
| OP1.5 | 5.785 | | | | | E |

Grouping of infiltration conditions based on GFP concentration in percentage of TSP concentration using each pairs student t test with a confidence interval of 95% (levels not connected by the same letter are significantly different).

Conclusions

Efficiency of overpressures between 2.0 and 3.0 bars for Agro-infiltration of whole *N. benthamiana* plants and transient expression of recombinant TurboGFP approaches that of the currently used method of vacuum infiltration when the biomass used has reached the developmental stage currently used for Agro-infiltration (stage 10, 5-6 week-old plants, height of around 15 cm, well expanded leaves and maximum one flower open). Efficiency of infiltration by overpressure was lower than that of infiltration by vacuum when overpressures of 1.5 bar or lower were used or when the plants used for infiltration were at a younger developmental stage i.e. stage 8.

No adverse effect in terms of visible signs of plant stress of using positive pressures as high as 3.5 bar were observed during recovery and incubation post-infiltration.

Given the possibility to use purpose-built equipment, overpressure has the potential to considerably reduce infiltration cycle time as the overpressure brought to the tank by compressed air and the infiltration itself are almost instantaneous (here the positive pressure was maintained for 10 sec) whilst a complete vacuum cycle takes on average 4 to 5 minutes.

The addition of 0.01% triton to the infiltration solution did not improve the efficiency of the infiltration by overpressure at the pressure tested of 2.5 bar. However, use of this detergent at the same concentration during vacuum infiltration led to a significant increase of the expression of GFP in infiltrated leaves.

Part B

Infiltration Using Positive Pressure with *Nicotiana tabacum*

Example 10

Procedure and Method

A direct comparison of vacuum infiltration and the methods of the invention using positive pressure was conducted for the three tobacco varieties. In this experiment a total of 150 tobacco plants (50 per each tobacco variety) were germinated and grown under standard greenhouse conditions: 24° C. and 20 hours light. *N. tabacum* plants were transformed with *Agrobacterium* cultures (Agl1) containing the green fluorescent protein TurboGFP in combination with a suppressor of silencing (SoS) from a tobacco virus. Vacuum infiltration was applied using a commonly used set of conditions (50 mbar, 60 seconds holding time) and 7 different positive pressure conditions. Particularly, two factors—the positive pressure values [1.5-4.5 bar] and the number of pressure cycles ("pulses") [1-8] were tested while the pressure holding time/pulse was kept to 1 second to keep the total process time to its minimum.

Infiltrated plants were harvested 5 days after infiltration and GFP expression analyzed qualitatively and quantitatively. Qualitative estimations of GFP were performed by photographing the leaves after infiltration under blue light. Quantitative analysis of GFP abundance in leaves was determined by fluorescence measurement on a Modulus microplate reader (Turner Biosystems) in Fluorescence mode with Blue optical kit (Ex: 490 nm/Em: 510-570 nm). Leaf disks of approximately 80 mg were collected with a hole puncher from three leaves per plant (fully expanded leaves from positions 1-3, were 0 represents the shoot apical meristem) for all the treated plants. Samples from the three leaves of a single plant were pooled then ground in a TissueLyser (Qiagen) for approximately 2.5 minutes in the presence of 1 mL of GFP extraction buffer (50 mM Tris, 1 mM EDTA, 100 mM NaCl, 0.2% Triton X-100, pH 7.5). 10 µL of the supernatant was diluted 1:20 with the GFP extraction buffer and fluorescence quantified. GFP concentration was calculated using a standard curve made with commercial Evrogen tGFP protein. The standard curve was prepared by adding different amounts of TurboGFP control protein (Turbo GFP, Evrogen #FP552) to GFP-free leaves extracts diluted 1:40 in extraction buffer.

10.1 Results

A separate two-way ANOVA for each variety was conducted to test the equality of Fluorescence means and to check if there is significant evidence of interactions and main effects. No significant evidence of a Pressure*Pulses interaction for an alpha level of 0.05 (standard level of risk for type I error), but significant evidence of Pressure and Pulses main effects for plant 1 and plant 2, and only of Pressure main effect for plant 3. The additive model was also calculated, omitting the interaction term from the model, but with no relevant difference. Plant 1 exhibited a significantly higher difference between the Fluorescence means for a pressure of 4.5 bars and a cycle of 8 pulses.

A simple ANOVA was used to compare Fluorescence measurements from the optimal conditions with the reference measurements obtained using the vacuum method (see Table 11). It is inferred for plant 2 from the p-value and the amount of variation in the observed response values (R2 and adjusted R2—see table 10) that there is statistically significant differences with the reference.

TABLE 11

|  | Source | DF | SS | MS | F | P |
|---|---|---|---|---|---|---|
| Plant 3 | Pressure | 1 | 1103834 | 1103834 | 0.10 | 0.754 |
| vs | Error | 8 | 84243951 | 10530494 |  |  |
| Reference | Total | 9 | 85347785 |  |  |  |
|  | S = 3245 R-Sq = 1.29% R-Sq(adj) = 0.00% | | | | | |
| Plant 1 | Pressure | 1 | 69691378 | 69691378 | 1.21 | 0.308 |
| vs | Error | 7 | 403771649 | 57681664 |  |  |
| Reference | Total | 8 | 473463026 |  |  |  |
|  | S = 7595 R-Sq = 14.72% R-Sq(adj) = 2.54% | | | | | |
| Plant 2 | Pressure | 1 | 351389652 | 351389652 | 6.74 | 0.036 |
| vs | Error | 7 | 365030615 | 52147231 |  |  |
| Reference | Total | 8 | 716420267 |  |  |  |
|  | S = 7221 R-Sq = 49.05% R-Sq(adj) = 41.77% | | | | | |

The comparison is investigated further by taking confidence intervals for the difference between the means with a family error rate is 0.05 to control the rate of type I error. The intervals for pressures 0.05 (vacuum) and 4.5 (overpressure) both have zero as an end point, indicating that these differences are significant with overpressure being the best in this specific case.

TABLE 12

| Plant 2 optimal conditions vs Reference | Level | Lower | Center | Upper | --------+--------+--------+--------+- |
|---|---|---|---|---|---|
|  | 0.05 | -21753 | -12575 | 0 | (--------*---------) |
|  | 4.50 | 0 | 12575 | 21753 | (---------*-------) |
|  |  |  |  |  | --------+--------+--------+--------+- |
|  |  |  | -12000 | 0 12000 24000 | |

The above observations are confirmed by the qualitative GFP quantitation where it can be visually perceived that higher pressure and increased number of pulses lead to higher GFP expression.

Figure 2:
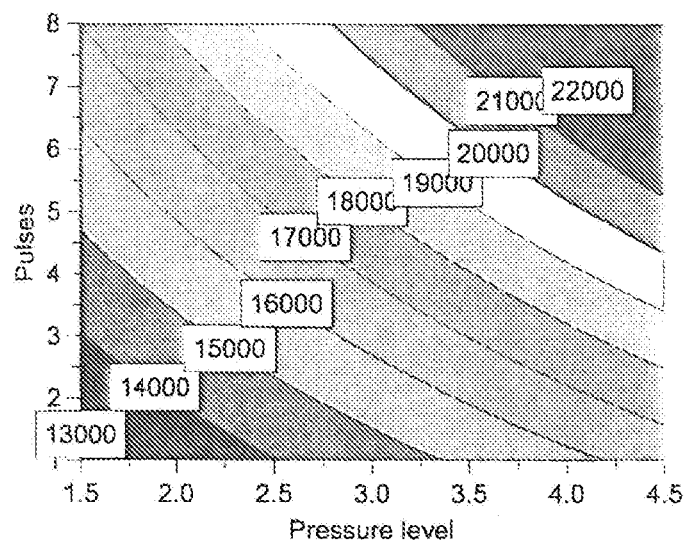
FIG. 2 shows a 2D contour plot over actual range for Fluorescence response values (PMF015).
Figure 3:
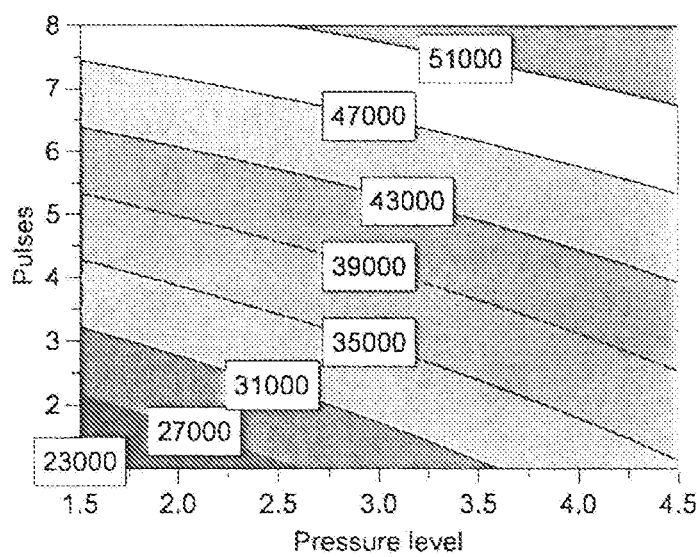
FIG. 3 shows a 2D contour plot over actual range for Fluorescence response values (PMF132).
Figure 4:
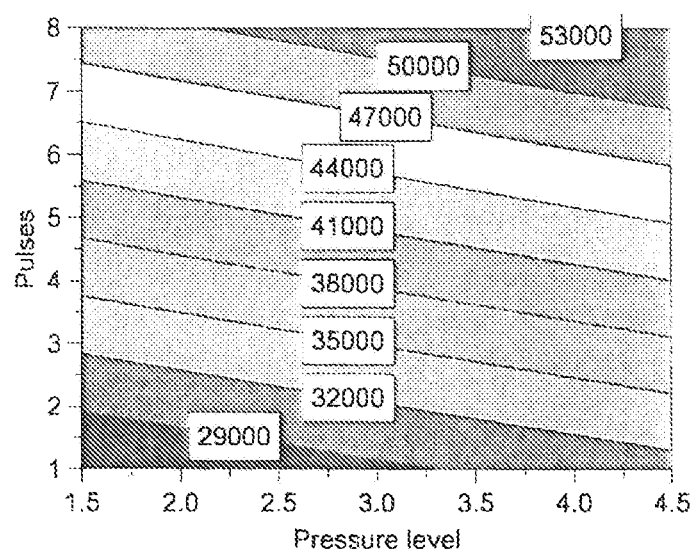
FIG. 4 shows a 2D contour plot over actual range for Fluorescence response values (PMF204).
Figure 5:
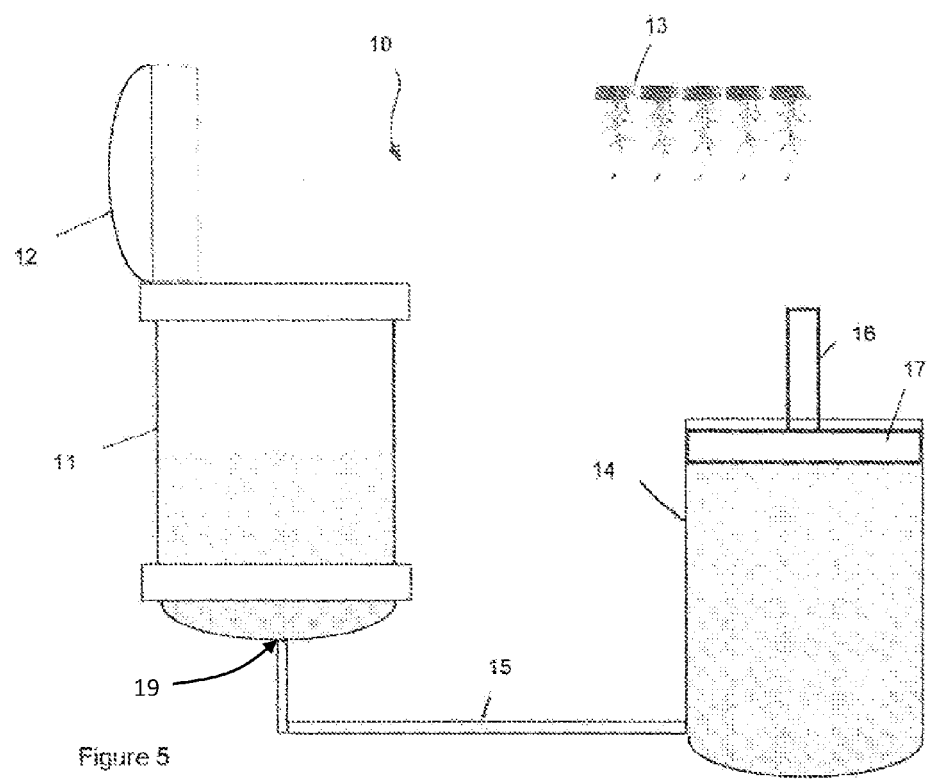
FIG. 5 shows a schematic view of a system for infiltrating *Agrobacterium* bacteria into a whole and intact plant under pressure.
Figure 6:
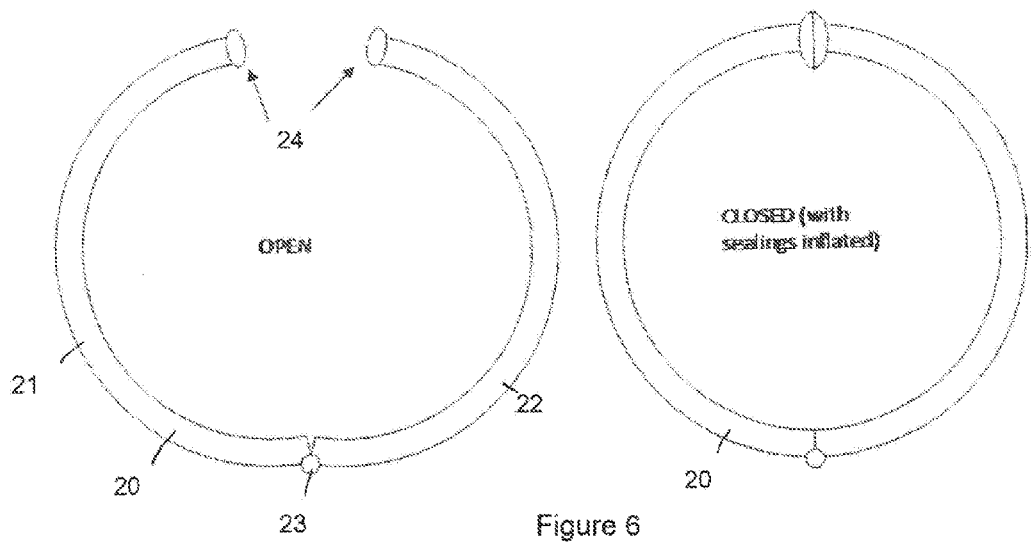
FIG. 6 shows a schematic cross sectional view of a chamber 20.
Figure 7:
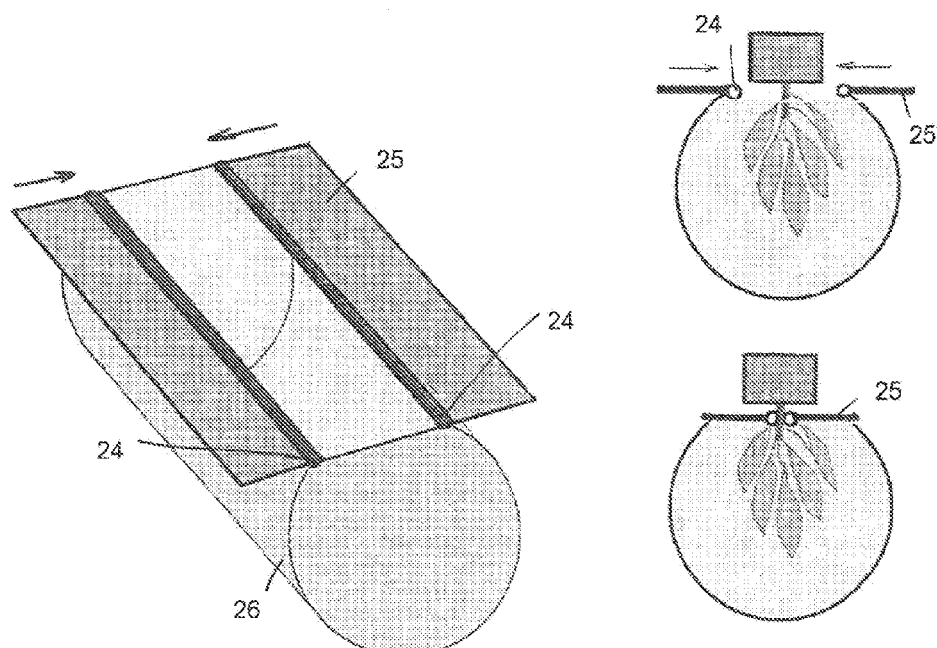
FIG. 7 shows a perspective schematic view of the chamber 26.

The 2D contour plots shown in FIGS. 2, 3 and 4 displayed the predicted Fluorescence response values, spanned by two factors, in a response contour plot, over the same range as the experiment (i.e. no outer-range predictions).

10.2 Conclusions

The data show significantly higher measurements of Fluorescence for plant 2 at an overpressure of 4.5 bars and a cycle of 8 pulses, compared to measurements obtained by using the vacuum method. The three *N. tabacum* varieties show increasing Fluorescence measurements when increasing the pressure and the pulses, which lead to the conclusion that increasing pressure and the number of pressure cycles can improve infiltration efficiency.

The invention claimed is:

1. A system for infiltrating *Agrobacterium* bacteria into a whole and intact plant or a part of a whole and intact plant and/or for producing a heterologous peptide or protein in a whole and intact plant or a part of a whole and intact plant comprising:
   a) a chamber defining an interior and comprising
      (i) an inlet in communication with the interior of the chamber;
      (ii) an opening lined with an elastic seal;
      (iii) an outlet in communication with the interior of the chamber; and
   b) a source of compressed air operably coupled to the inlet,
   wherein said chamber is configured for receiving through the opening all or part of areal parts of a plant and wherein the elastic seal is configured such that a seal can be formed around the main stem of the plant such that all or part of the aerial parts of a plant is positioned inside the chamber.

2. The system of claim 1, comprising a compressor and a pressure reducer configured to subject pressure to the whole and intact plant or a part of the whole and intact plant and *Agrobacterium* cells in suspension during one or more pressure cycle(s).

3. The system of claim 1, wherein the chamber comprises, in the interior, a plurality of nozzles that are dimensioned for atomizing or aerosolizing a liquid.

4. The system of claim 2, wherein the chamber is configured such that the entire plant body including its aerial and underground parts is submerged in the infiltration medium containing the *Argobacterium* cells and subjected to the pressure applied during the one or more pressure cycle(s).

5. The system of claim 2, wherein the chamber is configured such that only all or part of the aerial parts of the plant are submerged in the infiltration medium containing the *Argobacterium* cells, but the entire plant including the aerial parts as well as the underground parts of the plant is subjected to the pressure applied during the one or more pressure cycle(s).

6. The system of claim 2, wherein the chamber is configured such that all or part of the aerial parts of the plant are submerged in the infiltration medium containing the *Argobacterium* cells and exposed to pressure in the one or more pressure cycles, whereas the underground parts of the plant, particularly the plant root, are positioned outside of the chamber such that they are not submerged in the infiltration medium containing the *Agrobacterium* cells and not subjected to the pressure applied during the one or more pressure cycle(s).

7. The system of claim 1, wherein said elastic seal is an elastic pneumatic or hydraulic seal.

8. Use of a system according to claim 1 for infiltrating *Agrobacterium* bacteria into a whole plant or a plant part and/or for producing a heterologous peptide or protein in a whole plant or a plant part comprising:
   a) contacting within the chamber the aerial parts of a whole and intact plant, or a part of the aerial parts of a whole and intact plant, with *Agrobacterium* cells suspended in a fluid, wherein the *Agrobacterium* cells comprise an expressible construct encoding the heterologous peptide or protein of interest;
   b) treating the aerial parts of the whole and intact plant or a part of the aerial parts of the whole and intact plant and the *Agrobacterium* cells with one or more pressure cycle(s).

9. The use according to claim 8, wherein the expressible construct is a plant expressible construct and is selected to provide transient expression of the heterologous peptide or protein of interest.

10. The use according to claim 8 further comprising applying pressure to the whole and intact plant or a part of the whole and intact plant, while said plant or plant part is in contact with the *Agrobacterium* cells in the bacterial cell suspension.

11. The use according to claim 8, wherein the suspension of *Agrobacterium* cells comprises an OD600 of at least 1.0.

12. The use according to claim 8, wherein the chamber is configured such that the entire plant body including its aerial and underground parts is submerged in the infiltration medium containing the *Argobacterium* cells and subjected to the pressure applied during the one or more pressure cycle(s).

13. The use according to claim 8, wherein the chamber is configured such that only all or part of the aerial parts of the plant is submerged in the infiltration medium containing the *Argobacterium* cells, but the entire plant including the aerial parts as well as the underground parts of the plant is subjected to the pressure applied during the one or more pressure cycle(s).

14. The use according to claim 8, wherein the chamber is configured such that all or part of the aerial parts of the plant are submerged in the infiltration medium containing the *Argobacterium* cells and exposed to pressure in the one or more pressure cycles, whereas the underground parts of the plant, particularly the plant root, are positioned outside of the chamber such that they are not submerged in the infiltration medium containing the *Agrobacterium* cells and not subjected to the pressure applied during the one or more pressure cycle(s).

15. The use according to claim 8, wherein the step of treating the whole plant or the plant part comprises
   a) at least 2 cycles; or
   b) at least 3 cycles; or
   c) at least 4 cycles; or
   d) at least 8 cycles.

16. The use according to claim 8, wherein at least one of the pressure cycles comprises treating the whole plant or the plant part with a pressure of
   a) at least 3.5 bar; or
   b) at least 4.5 bar; or
   c) at least 6.5 bar; or
   d) at least 8 bar; or
   e) at least 12 bar.

17. The use according to claim 8, wherein the pressure is applied for between
   a) 0.5 seconds/cycle and 10 seconds/cycle; or
   b) 1 second/cycle and 5 seconds/cycle; or
   c) 0.5 seconds/cycle and 1 second/cycle.

18. The use according to claim 8, wherein the step of treating the whole plant or the plant part with a pressure that is increased relative to atmospheric pressure comprises
   a) at least 1 cycle, at a pressure of at least 8 bar, for at least 0.5 seconds/cycle; or
   b) at least 2 cycles, at a pressure of at least 6 bar, for at least 0.5 seconds/cycle; or
   c) at least 8 cycles, at a pressure of at least 4.5 bar, for at least 1 second/cycle.

19. The use according to claim 8, wherein the step of treating the whole plant or the plant part with a pressure that is increased relative to atmospheric pressure comprises at least 8 cycles, at a pressure of at least 4.5 bar, for at least 1 second/cycle.

20. The use according to claim 8, wherein the step of contacting the whole plant, or the plant part with *Agrobacterium* cells comprises
   a) dipping the plant or a part thereof in a suspension of *Agrobacterium* cells, wherein the suspension comprises an OD600 of at least 2.5,
   b) exposing the plant or a part thereof to an aerosol generated by using a suspension of *Agrobacterium* cells comprising an OD600 of at least 2.5.

21. The use according to claim 8, wherein the step of contacting the whole plant, or the plant part with *Agrobacterium* cells comprises
   a) submerging the plant or a part thereof in a suspension of *Agrobacterium* cells in an enclosed chamber, and
   b) applying liquid fluid pressure to the suspension of *Agrobacterium* cells comprising the submerged plant or part thereof.

22. The use according to claim 8, wherein the plant is a *Nicotiana* species, particularly a *Nicotiana tabacum* species, at a development stage of 8, 9, or 10, wherein the plants have an average height of between about 6.5 cm and about 16.5 CM.

23. The use according to claim 8, wherein all the pressure cycles applied comprise an increase in pressure relative to atmospheric pressure.

24. The use according to claim 8, wherein the pressure treatment comprising one or more pressure cycle(s) is applied while the whole and intact plant or a part of the whole and intact plant are submerged in the bacterial cell suspension.

* * * * *